US010232028B2

(12) United States Patent
Dahl

(10) Patent No.: US 10,232,028 B2
(45) Date of Patent: *Mar. 19, 2019

(54) COMPOUNDS AND METHODS FOR AFFECTING CYTOKINES

(71) Applicant: Zivo Bioscience, Inc., Keego Harbor, MI (US)

(72) Inventor: Andrew Dahl, Bloomfield Hills, MI (US)

(73) Assignee: ZIVO BIOSCIENCE, INC., Keego Harbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/898,091

(22) PCT Filed: Jun. 13, 2014

(86) PCT No.: PCT/US2014/042331
§ 371 (c)(1),
(2) Date: Dec. 11, 2015

(87) PCT Pub. No.: WO2014/201372
PCT Pub. Date: Dec. 18, 2014

(65) Prior Publication Data
US 2016/0120970 A1     May 5, 2016

Related U.S. Application Data

(63) Continuation of application No. 61/834,842, filed on Jun. 13, 2013.

(51) Int. Cl.
| | |
|---|---|
| *A61K 39/00* | (2006.01) |
| *A61K 39/02* | (2006.01) |
| *A61K 39/295* | (2006.01) |
| *A61K 39/09* | (2006.01) |
| *A61K 36/02* | (2006.01) |
| *A61K 36/06* | (2006.01) |
| *A61K 35/74* | (2015.01) |
| *A61K 36/10* | (2006.01) |
| *A61K 35/744* | (2015.01) |
| *A61K 39/108* | (2006.01) |

(52) U.S. Cl.
CPC ............ *A61K 39/092* (2013.01); *A61K 35/74* (2013.01); *A61K 35/744* (2013.01); *A61K 36/02* (2013.01); *A61K 36/06* (2013.01); *A61K 36/10* (2013.01); *A61K 39/0258* (2013.01); *A61K 39/09* (2013.01)

(58) Field of Classification Search
CPC ........ A61K 35/66; A61K 36/00; A61K 38/00; A61K 39/00
USPC .................. 424/9.1, 9.2, 184.1, 203.1, 234.1
See application file for complete search history.

(56) References Cited

U.S. PATENT DOCUMENTS

| | | | |
|---|---|---|---|
| 4,012,504 | A | 3/1977 | Eckols |
| 4,303,409 | A | 12/1981 | Ogawa et al. |
| 4,471,055 | A | 9/1984 | Opp |
| 4,822,612 | A | 4/1989 | Shinpo |
| 5,726,063 | A | 3/1998 | Gerard-Monnier et al. |
| 5,767,095 | A | 6/1998 | Winget |
| 6,235,495 | B1 | 5/2001 | Fu et al. |
| 6,374,874 | B1 | 4/2002 | Payne |
| 6,461,607 | B1 | 10/2002 | Farmer |
| 6,551,596 | B2 | 4/2003 | Kralovec |
| 6,673,908 | B1 | 1/2004 | Stanton |
| 6,733,751 | B2 | 5/2004 | Farmer |
| 7,025,965 | B1 | 4/2006 | Pieloch |
| 7,125,846 | B2 | 10/2006 | Rojkjaer |
| 7,807,622 | B2 | 10/2010 | Thomas et al. |
| 8,586,053 | B2 * | 11/2013 | Thomas ............... A61K 31/715 424/195.17 |
| 8,791,060 | B2 * | 7/2014 | Thomas ............... A61K 31/715 514/1 |
| 9,486,005 | B2 | 11/2016 | Gupta et al. |
| 2002/0009479 | A1 | 1/2002 | Vardi et al. |
| 2002/0119164 | A1 | 8/2002 | Uchiyama et al. |
| 2003/0015587 | A1 | 8/2003 | Kralovec |
| 2003/0152587 | A1 | 8/2003 | Kralovec |
| 2005/0114920 | A1 | 5/2005 | Yusibov et al. |
| 2005/0229585 | A1 | 10/2005 | Webster |
| 2005/0260695 | A1 | 11/2005 | Flemming et al. |
| 2006/0101803 | A1 | 5/2006 | White |
| 2007/0010480 | A1 | 1/2007 | Rusing et al. |

(Continued)

FOREIGN PATENT DOCUMENTS

| | | |
|---|---|---|
| CA | 2564466 | 12/2005 |
| CA | 2485449 | 4/2006 |

(Continued)

OTHER PUBLICATIONS

USPTO; Advisory Action dated Mar. 6, 2009 in U.S. Appl. No. 11/606,676.
USPTO; Final Office Action dated May 29, 2009 in U.S. Appl. No. 11/606,676.
USPTO; Final Office Action dated Nov. 14, 2008 in U.S. Appl. No. 11/606,676.
USPTO; Office Action dated Feb. 4, 2008 in U.S. Appl. No. 11/606,676.
USPTO; Office Action dated Oct. 8, 2009 in U.S. Appl. No. 11/606,676.
USPTO; Notice of Allowance dated May 27, 2010 in U.S. Appl. No. 11/606,676.

(Continued)

*Primary Examiner* — Rodney P Swartz
(74) *Attorney, Agent, or Firm* — Snell & Wilmer L.L.P.

(57) ABSTRACT

The present invention discloses isolates and fractions from a phyto-percolate and methods for affecting various cytokines by administering an effective amount of one or more of said isolates or fractions to an animal. In various exemplary embodiments, the isolates are useful for the treatment of bovine, canine and swine infection or inflammation, including bovine mastitis, by regulation of TNF-a, lactoferrin, IFN-γ, IL-I β, serum amyloid-A (SAA), IL-6 and/or β-defensin associated with infection or an immune response generally.

14 Claims, 18 Drawing Sheets

(56) References Cited

U.S. PATENT DOCUMENTS

| | | | |
|---|---|---|---|
| 2007/0207231 | A1 | 9/2007 | Thomas et al. |
| 2008/0089843 | A1 | 4/2008 | Pillarisetti et al. |
| 2008/0119571 | A1 | 5/2008 | Khanna et al. |
| 2008/0272232 | A1 | 11/2008 | Cagle et al. |
| 2008/0272615 | A1 | 11/2008 | McKnight et al. |
| 2009/0036372 | A1 | 2/2009 | Thomas et al. |
| 2009/0117216 | A9 | 5/2009 | Thomas et al. |
| 2010/0028488 | A1 | 2/2010 | Lo et al. |
| 2011/0081319 | A1* | 4/2011 | Thomas ............... A61K 31/715 424/93.4 |
| 2011/0117122 | A1 | 5/2011 | Thomas et al. |
| 2011/0124544 | A1 | 5/2011 | He et al. |
| 2011/0143012 | A1 | 6/2011 | Rettenmaier |
| 2011/0307976 | A1 | 12/2011 | Ploechinger |
| 2012/0328598 | A1 | 12/2012 | Gupta et al. |
| 2013/0251698 | A1 | 9/2013 | Thomas et al. |
| 2015/0157688 | A1 | 6/2015 | Thomas et al. |
| 2017/0135391 | A1 | 5/2017 | Gupta et al. |
| 2017/0360883 | A9 | 12/2017 | Thomas et al. |
| 2018/0021392 | A1 | 1/2018 | Dahl et al. |
| 2018/0255820 | A1 | 9/2018 | Dahl |

FOREIGN PATENT DOCUMENTS

| | | | |
|---|---|---|---|
| CN | 2827401 | 8/2011 | |
| CN | 102225127 | 10/2011 | |
| EP | 1230927 | 8/2002 | |
| EP | 1230927 A1 * | 8/2002 | ............ A61K 36/28 |
| EP | 1878877 | 1/2008 | |
| EP | 1928247 | 10/2009 | |
| EP | 2501390 | 9/2012 | |
| EP | 2538951 | 1/2013 | |
| JP | 0940523 | 2/1997 | |
| JP | 2009518312 | 5/2009 | |
| JP | 2014006051 | 1/2014 | |
| WO | 2011060427 | 5/2001 | |
| WO | 2003028749 | 4/2003 | |
| WO | 2005112987 | 12/2005 | |
| WO | 2006055217 | 5/2006 | |
| WO | 2006113925 | 10/2006 | |
| WO | 2007065024 | 6/2007 | |
| WO | 2011016973 | 2/2011 | |
| WO | 2011103569 | 8/2011 | |
| WO | 2014201372 | 12/2014 | |
| WO | 2016133922 | 8/2016 | |
| WO | 2017142906 | 8/2017 | |
| WO | 2018165205 | 9/2018 | |

OTHER PUBLICATIONS

USPTO; Examiner Interview Summary Record dated Apr. 12, 2010 in U.S. Appl. No. 11/606,676.
USPTO; Final Office Action dated Nov. 3, 2008 in U.S. Appl. No. 11/587,266.
USPTO; Non-Final Office Action dated Feb. 4, 2008 in U.S. Appl. No. 11/587,266.
USPTO; Office action dated Oct. 22, 2012 in U.S. Appl. No. 12/067,735.
USPTO; Requirement for Restriction dated Oct. 19, 2010 in U.S. Appl. No. 12/067,735.
USPTO; Requirement for Restriction dated Jul. 20, 2011 in U.S. Appl. No. 12/067,735.
USPTO; Office Action dated Mar. 13, 2012 in U.S. Appl. No. 12/067,735.
USPTO; Final Office Action dated Oct. 23, 2012 in U.S. Appl. No. 12/067,735.
USPTO; Notice of Allowance dated May 13, 2013 in U.S. Appl. No. 12/067,735.
USPTO; Notice of Allowance dated Aug. 15, 2013 in U.S. Appl. No. 12/067,735.
USPTO; Advisory Action dated Feb. 26, 2014 in U.S. Appl. No. 12/897,574.
USPTO; Non-Final Office Action dated Jun. 24, 2013 in U.S. Appl. No. 12/897,574.
USPTO; Final Office Action dated Nov. 13, 2013 in U.S. Appl. No. 12/897,574.
USPTO; Notice of Allowance dated Apr. 8, 2014 in U.S. Appl. No. 12/897,574.
USPTO; Final Office Action dated May 21, 2012 in U.S. Appl. No. 12/947,684.
USPTO; Final Office Action dated Oct. 9, 2013 in U.S. Appl. No. 12/947,684.
USPTO; Office Action dated Sep. 9, 2011 in U.S. Appl. No. 12/947,684.
USPTO; Office Action dated Dec. 20, 2012 in U.S. Appl. No. 12/947,684.
USPTO; Advisory Action dated Aug. 7, 2015 in U.S. Appl. No. 13/580,471.
USPTO; Final Office Action dated Apr. 2, 2015 in U.S. Appl. No. 13/580,471.
USPTO; Office Action dated Aug. 26, 2014 in U.S. Appl. No. 13/580,471.
USPTO; Notice of Allowance dated Jun. 20, 2016 in U.S. Appl. No. 13/580,471.
USPTO; Restriction Requirement dated Mar. 4, 2014 in U.S. Appl. No. 13/580,471.
USPTO; Office Action dated Dec. 8, 2015 in U.S. Appl. No. 13/580,471.
USPTO; Office Action dated Jun. 2, 2014 in U.S. Appl. No. 13/841,739.
USPTO; Office Action dated Jun. 1, 2017 in U.S. Appl. No. 14/558,516.
USPTO; Notice of Allowance dated Jan. 12, 2018 in U.S. Appl. No. 14/558,516.
USPTO; Restriction Requirement dated Dec. 23, 2016 in U.S. Appl. No. 14/558,516.
USPTO; Restriction Requirement dated Dec. 18, 2012 in U.S. Appl. No. 13/397,360.
USPTO; Office Action dated Jun. 19, 2014 in U.S. Appl. No. 13/397,360.
USPTO; Restriction Requirement dated Apr. 20, 2018 in U.S. Appl. No. 15/550,749.
USPTO; Restriction Requirement dated Aug. 6, 2018 in U.S. Appl. No. 15/330,830.
USPTO; Notice of Allowance dated Aug. 27, 2018 in U.S. Appl. No. 14/558,516.
USPTO; Non-Final Office Action dated Sep. 17, 2018 in U.S. Appl. No. 15/550,749.
Australia: Examination Report dated Aug. 30, 2011 in International Application No. AU2006320264.
Australia: Examination Report dated Sep. 7, 2012 in International Application No. AU2006320264.
Australia: Examination Report dated Apr. 11, 2014 in International Application No. AU2013204257.
Canadian: Examination Report dated Feb. 26, 2015 in International Application No. CA2631773.
Canadian: Examination Report dated Mar. 31, 2016 in International Application No. CA2631773.
Canadian: Examination Report dated Apr. 2, 2014 in International Application No. CA2631773.
Canadian: Examination Report dated May 24, 2013 in International Application No. CA2631773.
Canadian: Examination Report dated May 16, 2017 in International Application No. CA2631773.
Canadian; Examination Report dated Jun. 27, 2018 in International Application No. CA2631773.
Canadian: Examination Report dated Mar. 28, 2017 in International Application No. CA2780144.
Canadian: Examination Report dated Aug. 15, 2016 in International Application No. CA2780144.
Canadian; Examination Report dated Mar. 29, 2018 in International Application No. CA2827401 (Aug. 29).
EPO: Extended Search Report/Written Opinion dated Nov. 2, 2017 in International Application No. EP20111745434.

(56) References Cited

OTHER PUBLICATIONS

EPO: Examination Report dated Mar. 22, 2012 in International Application No. EP2006320264.
EPO: Examination Report dated Oct. 13, 2009 in International Application No. EP2006320264.
EPO: Supplemental Search Report-Written Opinion dated Sep. 24, 2009 in International Application No. EP2006758513.
EPO; Examination Report dated Nov. 20, 2009 in International Application No. EP2006758513.
EPO; Examination Report dated Mar. 22, 2012 in International Application No. EP2006758513.
EPO: Examination Report dated Mar. 31, 2016 in International Application No. EP2010830908.
EPO: Extended Search Report dated Jun. 2, 2014 in International Application No. EP20100830908.
EPO: Office Action dated Feb. 23, 2010 in International Application No. EP2006838974.
EPO; Extended Search Report dated Aug. 10, 2018 in International Application No. EP16752918.9.
EPO; Supplementary Search Report dated Aug. 28, 2018 in International Application No. EP16752918.9.
Japan: Examination Report dated Aug. 7, 2012 in International Application No. JP200854345.
Japan: Examination Report dated Nov. 11, 2014 in International Application No. JP2012539974.
PCT: Search Report and Written Opinion dated Jul. 29, 2011 in International Application No. PCT/US2010056862.
PCT: International Preliminary Report on Patentability dated May 22, 2012 in International Application No. PCT/US2010056862.
PCT: Written Opinion dated Sep. 24, 2014 in International Application No. PCT/US2014042331.
PCT: International Search Report dated Sep. 24, 2014 in International Application No. PCT/US2014042331.
PCT: IPRP dated Dec. 15, 2015 in International Application No. PCT/US2014042331.
PCT: Written Opinion dated May 25, 2017 in International Application No. PCT/US2017017906.
PCT: International Search Report dated May 25, 2017 in International Application No. PCT/US2017017906.
PCT: Written Opinion dated Aug. 4, 2016 in International Application No. PCT/US2016018105.
PCT: International Search Report dated Aug. 4, 2016 in International Application No. PCT/US2016018105.
PCT: International Preliminary Report on Patentability dated Aug. 22, 2017 in International Application No. PCT/US2016018105.
PCT: Written Opinion dated Jun. 21, 2011 in International Application No. PCT/US2011025713.
PCT: International Search Report dated Jun. 21, 2011 in International Application No. PCT/US2011025713.
PCT: International Preliminary Report on Patentability dated Aug. 28, 2012 in PCT/US2011025713.
PCT: Written Opinion dated Dec. 6, 2005 for International Application No. PCT/US2005/013375.
PCT: International Preliminary Report on Patentability dated Oct. 25, 2006 for International Application No. PCT/US2005/013375.
PCT: Written Opinion dated Mar. 22, 2007 for International Application No. PCT/US2006/015302.
PCT: International Preliminary Report on Patentability dated Oct. 23, 2007 for International Application No. PCT/US2006/015302.
PCT: International Search Report dated Oct. 17, 2007 for International Application No. PCT/US2006/046320.
PCT: International Search Report dated Feb. 23, 2012 for International Application No. PCT/US2011/44786.
PCT: Written Opinion dated Feb. 23, 2012 for International Application No. PCT/US2011/44786.
PCT: International Preliminary Report on Patentability dated Jan. 29, 2013 for International Application No. PCT/US2011/44786.
PCT; International Search Report dated Jun. 28, 2018 in International Application No. PCT/2018/021215.
PCT; Written Opinion dated Jun. 28, 2018 in International Application No. PCT/US2018/021215.
Amaro et al., "Antimicrobial Activities of Microalgae: An Invited Review," Science Against Microbial Pathogens: Communicating Current Research and Technological Advances (Ed. Mendez-Vilas, A.), Formatex Research Center, Spain, ISBN-13: 978-84-939843-1-1, pp. 1272-1280, (2011).
Bhadury et al., "Exploitation of Marine Algae: Biogenic Compounds for Potential Antifouling Applications," Planta, (E-pub), vol. 219, No. 4, pp. 561-578, (Jun. 24, 2004).
Brewer et al., "Arteriosclerosis, Thrombosis, and Vascular Biology: Regulation of Plasma High-Density Lipoprotein Levels by the ABCA1 Transporter and the Emerging Role of High-Density Lipoprotein in the Treatment of Cardiovascular Disease," American Heart Association, vol. 24(24), pp. 1755-1760, (Aug. 19, 2004).
Fujita, "NF-KB: Regulation and Genetic Engineering of Signal Transduction of Inflammation," Journal of Clinical and Experimental Medicine, vol. 190(10), pp. 913-916, (1999).
Kim et al., "Purification and Characterization of a Fibrinolytic Enzyme Produced from *Bacillus* sp.strain CK 11-4 Screened from Chungkook-Jang," Environ. Microbiology, vol. 62, No. 7, pp. 2482-2488, (Jul. 1996).
Kim, Young-Gon, and Moon-Seog Jun, "A Design of User Authentication System Using QR Code Identifying Method," Computer Sciences and Convergence Information Technology (ICCIT), 6th International Conference on IEEE, (Nov. 29-Dec. 1, 2011).
Mudimu et al., "Biotechnological Screening of Microalgal and Cyanobacterial Strains for Biogas Production and Antibacterial and Antifungal Effects," Metabolites, vol. 4, No. 2, pp. 373-393, (May 15, 2014).
Noda et al., "A Water-Soluble Antitumor Glycoprotein from Chlorella Vulgaris," Faculty of Pharmaceutical Sciences, Kyushu University, (Oct. 1996) Abstract Only.
Oben et al., "The Effects of ProAlgaZyme Novel Algae Infusions on Metabolic Syndrome and Markers of Cardiovascular Health," Lipids in Health and Disease, vol. 6, pp. 1-9, (2007).
Oben et al., "Lipids in Health and Disease: The Effects of ProAlgaZyme Novel Algae Infusion of Metabolic Syndrome and Markers of Cardiovascular Health," BioMed Central, pp. 1-9, (Sep. 5, 2007).
Okada et al., "Inflammatory Bowel Disease and Cytokine," Journal of Clinical and Experimental Medicine, pp. 265-268, (Oct. 2004).
Press Release entitled, "Western Glory Hole Inc. Enters Definitive Agreement with Health Enhancement Products in," Business Wire, (Oct. 30, 2003).
Sarkar et al., "Using Chemopreventive Agents to Enhance the Efficacy of Cancer Therapy," Cancer Research, vol. 66(7), pp. 3347-3350, (Apr. 1, 2006).
"BioSuperfood-Algae/Spirulina for People," Optimum Choices, pp. 1-23, http://www.optimumchoices.com/spirulina.htm., (Apr. 14, 2010).
"Spirulina," MedlinePlus, U.S. National Library of Medicine and the National Institutes of Health, http://www.nlm.nih.gov/medlineplus/dniginfo/natural/patient-spirulina.html., (Apr. 14, 2010).
Gupta et al., "ProAlgaZyme and its Sub-Fractions Increase Plasma HDL-Cholesterol Via Up Regulation of ApoA1, ABCA1 and SRB1 and Inhibition of CETP in Hypercholesterolemic Hamsters," Journal of Nutrition and Food Science, WSU, (Jun. 2012).
www.michaelkiriac.com, (Jan. 1, 2003).
Health Enhancement Products, Inc., "Research Indicates ProAlgaZyme May Decrease Risk of Stroke or Heart Attack," Supplemental Quality.com, pp. 10, 11, (Jan. 20, 2004).

\* cited by examiner

Low Density

High Density

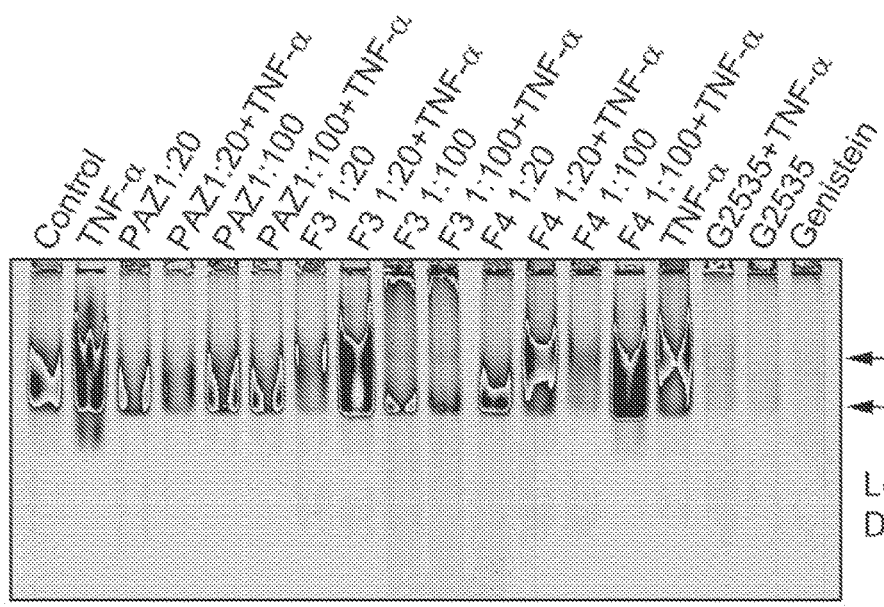
FIG.2C Low Density
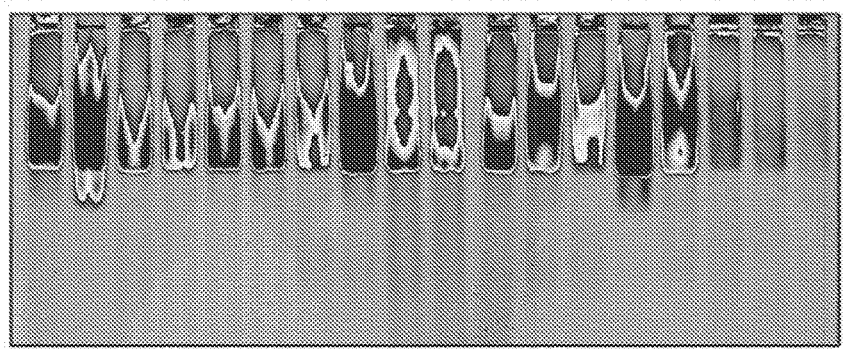
FIG.2D High Density

COMPOUNDS AND METHODS FOR AFFECTING CYTOKINES

CROSS REFERENCE TO RELATED APPLICATIONS

This application is a U.S. National Phase filing under U.S.C. § 371 of PCT Patent Application No. PCT/US2014/42331, filed Jun. 13, 2014, which claims priority to U.S. Provisional Patent Application Ser. No. 61/834,842 filed Jun. 13, 2013, which are incorporated herein by reference in their entirety.

FIELD OF THE INVENTION

This invention generally relates to compounds and methods for altering the production and/or function of proteins such as cytokines and transcription factors. More specifically, the present invention relates to a composition derived from a culture or co-culture of specific freshwater microorganisms, algae, moss, bacteria and/or fungi, the isolation of fractions and compounds therefrom, and methods of treating or preventing inflammation and/or diseases such as bovine mastitis, bovine respiratory disease complex, transition cow syndrome, canine osteoarthritis, canine skeletal-muscular overexertion and porcine reproductive and respiratory syndrome virus immune disorder, by administering an effective amount of the composition, fractions or compounds isolated therefrom.

BACKGROUND OF THE INVENTION

Cytokines are a broad class of proteins that are secreted by various cell types, including cells of the immune system. One function of cytokines is to carry various signals between cells and thus control activity among cells. Several factors can cause cells to secrete cytokines, including a cell's encounter with pathogens that may cause disease. In certain instances, cells will secrete cytokines as a means of organizing a natural defense against the pathogen or disease.

There are numerous cytokines, such as interleukins ("IL") produced by white blood cells. Individual interleukins include, for example, IL-2, IL-10, and IL-17A. Each of these interleukins have specific functions and effects, such as decreasing or increasing inflammation, stimulating the proliferation and function of various cell types, and regulating the production of antibodies. For example, IL-2 contributes toward inflammation and may be considered as inflammatory proteins, while IL-10 may be considered an anti-inflammatory protein that decreases inflammation. Therefore, the more IL-2 produced, the greater the inflammation and the more IL-10 produced the lesser the inflammation.

Interleukins have been determined to be involved in many processes, including, but not limited to, inflammation. For example, there is substantial evidence suggesting that IL-2 suppresses the production of immunoglobulins. In contrast, there is substantial evidence suggesting that IL-10 enhances immunoglobulin production.

Another cytokine is interferon-gamma or IFN-γ. IFN-γ is critical for innate and adaptive immunity against viral and intracellular bacterial defense functions and for tumor control. IFN-γ has been shown to alter the transcription of over thirty genes and to produce such affects as increasing T-helper (Th2) cell activity, promoting natural killer (NK) cell activity, and affecting various other molecular signaling pathways.

Other cytokines include tumor necrosis factor (TNF) alpha, or TNF-α, which is involved in the regulation of immune cells. Further, elevated production of TNF-α has been implicated as a contributing factor in a variety of human diseases, including cancer. TNF-α contributes to inflammation and may be considered an inflammatory protein. The more TNF-α produced, the greater the inflammation.

Yet another cytokine is granulocyte-macrophage colony-stimulating factor or GM-CSF. GM-CSF is a white blood cell growth factor that is known to stimulate stem cells, and is part of the immune/inflammatory cascade.

A transcription factor known as "nuclear factor kappa beta" or NF-κB is an intracellular protein that functions as a regulator of gene transcription and plays an important role in various biological processes and pathology. NF-κB has been found to play an important role in regulating the immune system in response to infection, and in several inflammatory pathways including the production of cyclooxygenase, nitric oxide synthase and other pro-inflammatory proteins. Inappropriate regulation of NF-κB has been linked to cancer, inflammatory and autoimmune diseases, septic shock, viral infection, and improper immune development and certain studies have linked NF-κB to processes involving synaptic plasticity and memory. The role of NF-κB and various cytokines is discussed in the article entitled *Using Chemopreventive Agents to Enhance the Efficacy of Cancer Therapy*, by Sarkar, et al., and published by the American Association for Cancer Research on Apr. 1, 2006, which is herein incorporated by reference in its entirety. Further, various viruses, including the HIV virus have molecular binding sites for NF-κB, thus indicating the NF-κB may be a critical component for activating the HIV virus from a latent state to an active state.

Therefore, the regulation of cytokines and/or transcription factors such as NF-κB can be a critical process in providing treatment for various ailments. For example, since IL-10 has anti-inflammatory properties, increasing IL-10 in a patient suffering from a chronic inflammatory condition can be used to treat the inflammation. Alternatively, since NF-κB is a factor for activating the HIV virus from a latent state to an active state, reducing the amount of NF-κB could delay or prevent the HIV virus from being activated.

Although there are known compositions and methods for regulating cytokines and NF-κB, many of these known compositions and methods are irritating to cells or have a toxic effect on cells. Further, many known compositions and methods for regulating cytokines and NF-κB regulate many cytokines in the same manner, some of which may hinder the overall desired effect of the treatment. For example, there are known compositions and methods for treating inflammation that up-regulate anti-inflammatory cytokines such as IL-10, but these compositions also result in up-regulation of IL-2, an inflammatory cytokine that reduces the effect of the IL-10.

Therefore, it would be advantageous to provide improved compounds, compositions and methods of regulating anti-inflammatory cytokines and transcription factors such as NF-κB on a cellular level. Moreover, providing compounds, compositions and methods that could regulate selected cytokines and transcription factors NF-κB to achieve a multitude of effects for the treatment of various health problems would be desirable. One example of such specific regulation of multiple cytokines would be selected compounds or a composition that up-regulates IL-10 without up-regulating IL-2, or even while down-regulating IL-2, thus increasing anti-inflammatory cytokines while reducing or maintaining the level of pro-inflammatory cytokines in order to reduce inflammation. It would also be desirable to provide selected compounds, compositions, and methods to affect various cytokines and transcription factors such as NF-κB that are not irritants, are non-toxic, easy to manufacture and distribute, and not expensive to produce, isolate and purify.

SUMMARY OF THE INVENTION

As set forth in the detailed description and in accordance with various embodiments of the present invention, selected compounds, compositions and methods for effecting cytokines and transcription factors such as NF-κB is disclosed.

According to one exemplary embodiment, a composition is derived from the culture or co-culture of specific freshwater microorganisms, algae, moss, bacteria and/or fungi of ATCC Deposit No. PTA-5863.

In various other embodiments, isolates, such as purified compounds, mixtures of compounds and fractions, are derived from the culture or co-culture.

According to various exemplary embodiments of the present invention, a method of effecting cytokines and transcription factors such as NF-κB to regulate immune response, reduce inflammation, provide antioxidant activity, modulate antibody production, treat or prevent cancerous tumor growth, and treat or prevent infections including HIV is disclosed.

In various embodiments, a composition is non-toxic and capable of selectively up-regulating certain cytokines, such as IL-10, while maintaining or reducing other cytokines, such as IL-2 and/or TNF-α, to achieve a desired result, such as reduced inflammation.

In still yet other exemplary embodiments of the present invention, a method of affecting the DNA-binding activity of NF-κB and a method of reducing TNF-α-induced activation of NF-κB is disclosed. Further, according to various exemplary embodiments of the present invention, methods of inducing certain anti-inflammatory cytokines such as IL-10, particularly while not inducing other pro-inflammatory cytokines such as IL-2, TNF-α and IFN-γ is disclosed.

In various embodiments, isolates obtained from a culture or co-culture of specific freshwater microorganisms, algae, moss, bacteria and/or fungi are used for affecting cytokine levels in animal infections and inflammations, such as bovine mastitis, bovine respiratory disease complex, transition cow syndrome, canine osteoarthritis, canine skeletal-muscular overexertion and porcine reproductive and respiratory syndrome virus immune disorder, (PRRSV).

In various embodiments, a method of treating mastitis in a cow comprises administering to said cow a therapeutically effective amount of one or more isolates or fractions of phyto-percolate derived from culturing microorganisms of ATCC Deposit No. PTA-5863.

In various embodiments, isolates obtained from a culture or co-culture of specific freshwater microorganisms, algae, moss, bacteria and/or fungi are used for affecting levels of TNF-α, lactoferrin, IFN-γ, IL-1β, serum amyloid-A, IL-6 and β-defensin in primary bovine mammary epithelial cells subjected to pathogens or substances derived from pathogens.

In various embodiments, isolates obtained from a culture or co-culture of specific freshwater microorganisms, algae, moss, bacteria and/or fungi are used for modulating immune and/or inflammatory responses in animals and humans.

In various embodiments, a method of modulating an immune response in bovine, swine or canine comprises administering to said bovine, swine or canine an effective amount of one or more isolates or fractions of phyto-percolate derived from culturing microorganisms of ATCC Deposit No. PTA-5863. In various embodiments, the immune response may be triggered by, or characteristic of, bovine mastitis, bovine respiratory disease complex, transition cow syndrome, canine osteoarthritis, canine skeletal-muscular overexertion or porcine reproductive and respiratory syndrome virus immune disorder, (PRRSV).

In various embodiments, isolates obtained from a culture or co-culture of specific freshwater microorganisms, algae, moss, bacteria and/or fungi are used for affecting cytokine levels in canine infections and inflammations.

In various embodiments, isolates obtained from a culture or co-culture of specific freshwater microorganisms, algae, moss, bacteria and/or fungi are used for affecting cytokine levels in human infections and inflammations.

In various embodiments, a method of promoting an antimicrobial response at a site of infection in an animal comprises administering to said animal an effective amount of one or more isolates or fractions of phyto-percolate derived from culturing microorganisms of ATCC Deposit No. PTA-5863. In various embodiments, the animal is a cow, swine or canine. In various embodiments, the animal is a cow and the site of infection is bovine mammary tissue.

BRIEF DESCRIPTION OF THE DRAWINGS

The subject matter of the invention is particularly pointed out and distinctly claimed in the concluding portion of the specification. Embodiments of the invention, however, may best be understood by reference to the following detailed description taken in conjunction with the accompanying drawing figures, and wherein:

FIGS. 2A-2D illustrate raw data from electrophoretic gel mobility shift assays according to various exemplary embodiments of the present invention;

DETAILED DESCRIPTION OF THE INVENTION

Figure 1:
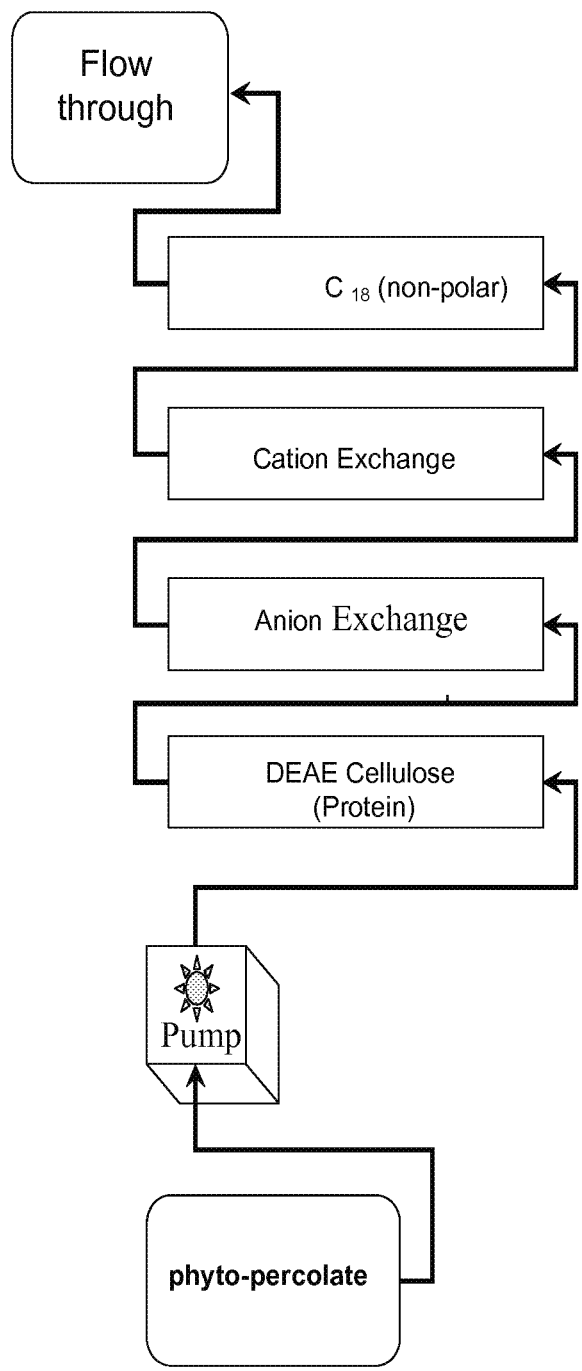
FIG. 1 illustrates a separation process usable for fractioning phyto-percolate or other culture or infusion into various fractions, components, and compounds.

The following description is of exemplary embodiments of the invention and is not intended to limit the scope or applicability of the invention in any way. Rather, the following description is intended to provide convenient illustrations for implementing various embodiments of the invention. Other configurations, compositions, amounts, and methods, and the like may be employed without departing from the scope of the present invention. As will become apparent, various other changes may be made to the methods described in these embodiments without departing from the spirit and scope of the invention.

According to various exemplary embodiments of the present invention, the present invention comprises administering compounds or compositions to affect various cytokines and transcription factors such as NF-κB. A composition usable to affect cytokines has been described in numerous commonly owned patents and co-pending patent applications including U.S. Pat. No. 7,807,622 entitled "Composition and Use of Phyto-Percolate For Treatment of Disease," U.S. Pat. No. 8,791,060 entitled "Composition and Use of Phyto-Percolate For Treatment of Disease," U.S. patent application Ser. No. 11/587,266 entitled "Method of Preparation and Use of Fibrinolytic Enzymes in the Treatment of Disease," U.S. Patent Application Ser. No. 61/306,591 entitled "Method of Lowering Cholesterol With PAZ Components," and U.S. Patent Application Ser. No. 61/311,838 entitled "Agents and Mechanisms for Treating Hypercholesterol with PAZ Components," all of which are herein incorporated by reference in their entirety. All foreign and PCT patent applications claiming priority to these U.S. applications are also incorporated herein by reference in their entirety.

The composition referred to herein as "phyto-percolate" is a non-toxic composition comprised generally of molecules produced by the culture or co-culture of specific microorganisms such as algae, moss, bacteria, and fungi. In one exemplary embodiment, a deposit of the culture used to create phyto-percolate has been placed in the American Type Culture Collection, 10801 University Blvd., Manassas, Va. 20110, on Mar. 17, 2004, as ACC Deposit No. PTA-5863. This deposit was made pursuant to 37 C.F.R. § 1.808 and MPEP § 2410.01 and therefore, access to the deposit will be available during pendency of this application making reference to the deposit to one determined by the Commissioner to be entitled thereto under 37 C.F.R. § 1.14 and 35 U.S.C. § 122 and with one exception, that all restrictions imposed by the depositor on the availability to the public of the deposited biological material be irrevocably removed upon granting of the patent.

In one exemplary embodiment, the composition described herein as "phyto-percolate" is created by the process set forth below. According to this embodiment, approximately one or more aliquots of the culture of the type currently on deposit as ATCC Deposit No. PTA-5863, are first obtained. In various embodiments where more than one aliquot is used, the aliquots may be combined in one larger composite culture vessel and maintained using the methods set forth below.

According to this exemplary embodiment, for each aliquot of culture obtained and cultured successfully from cryopreservation, the total volume is diluted using sterile deionized water to approximately 10 mL total volume (for example, 3 aliquots (~4.5 mL) are combined and diluted to 30 mL total volume). Further, a nutrient blend stock solution is prepared by mixing approximately 20 mg of dry active baker's yeast in approximately 1 mL warm sterile deionized water and then incubated for approximately 20 minutes at room temperature, yielding enough nutrient blend for approximately 1000 culture aliquots. Then, approximately 1 μL of the prepared nutrient blend is added to each diluted aliquot, (for example, to (3) combined and diluted aliquots, 3 μL prepared nutrient blend is added), and the mixture is then swirled gently.

The next step of producing phyto-percolate according to this exemplary embodiment comprises the step of incubating the culture sample with nutrient blend for approximately 1 week at room temperature in a sterilized culture vessel such as a round-bottom glass culture vessel with an ambient sterile-filtered air vent. In this exemplary embodiment, the mixture is swirled once half way through the week and maintained under approximately a 12:12 hour cycle of simulated daylight. After this week, approximately 1 µL freshly prepared nutrient blend is added to the culture vessel for approximately each diluted aliquot used, and this new mixture is preferably swirled gently. The culture sample with nutrient blend is incubated for approximately one additional week at room temperature and preferably swirled once half way through the week and maintained under a 12:12 hour cycle of simulated daylight.

Continuing with this exemplary method of producing phyto-percolate, the liquid volume is slowly drawn off or harvested using a sterile tubing and siphon or peristaltic pump from approximately the top half of the culture vessel, without disturbing the algal biomass growing in the bottom of the culture vessel, yielding approximately 5 mL per deposit aliquot used. The liquid may be reserved in a sterile glass storage container or another appropriate storage container, sterile-filtered and administered as desired. The liquid volume in the culture vessel should be replenished back to approximately its pre-harvested volume using sterile deionized room temperature water allowing the total final volume to be approximately 10 mL per deposit aliquot used. Approximately 1 µL of freshly prepared nutrient blend is then added to the culture vessel for approximately each aliquot used and then the mixture is swirled gently and allowed to incubate as described above in subsequent cycles as desired.

With continued reference to this exemplary embodiment, the culture sample and nutrient blend is incubated for approximately 1 week or more at room temperature while maintaining approximately a 12:12 hour cycle of stimulated daylight. While this culture is incubating with the nutrient blend, the previously harvested material is filtered through sterilizing membrane filters (or similar filters as those skilled in the art will recognize) with approximately a 0.2 µm pore size to generate the final bioactive liquid, described herein as 'composition' or 'phyto-percolate' or "PAZ." Any biomass captured in the filter may be destroyed or collected. Supplemental micronutrient or trace mineral blends specific to the needs of the culture may also be added to the culture during incubation or scale-up to preserve the integrity of the original culture biomass and to support further growth.

Further, according to this exemplary manufacturing method, once sufficient biomass has been generated over time in the culture (approximately 8 to 12 weeks or more), the culture may be split into 2 equal cultures as needed in a scale-up process by the following exemplary steps. First, homogenize the culture gently to fully suspend the biomass. Second, transfer approximately half of the homogeneous culture into a new sterilized glass or other appropriate culture vessel. Third, replenish the liquid volume in each of the two culture vessels back to original culture volume using sterile deionized water at room temperature. Fourth, add approximately 1 µL of freshly prepared nutrient blend to each culture vessel and swirl gently. Fifth, incubate the cultures with nutrient blend for approximately 1 week at room temperature, preferably swirling once half way through the week and maintaining them under the approximate 12:12 hour cycle of simulated daylight. Sixth, add approximately an additional 1 µL freshly prepared nutrient blend to the culture vessel. Seventh, incubate the culture sample with nutrient blend for approximately an additional week at room temperature, preferably swirling once half way through the week. Finally, with respect to this scale-up process, it should be noted that multiple cultures can be combined in larger culture vessels and maintained using the same general culturing methods and nutrient-to-culture volume ratios.

With continued reference to this exemplary embodiment of producing phyto-percolate, the steps noted above should be conducted as needed to generate a sufficient amount of phyto-percolate and its various derivatives. A sample of the phyto-percolate sold under the trademark PROALGAZME® may also be obtained from Health Enhancement Products, Inc. of Bloomfield Hills, Mich.

It should be noted that while specific examples have been given related to a method of producing a composition and quantities in the composition, that various modifications to the compositions and methods of producing the composition can be used and fall within the scope of the present invention. Further, it is contemplated and within the scope of the present invention that other culture methods, dilution volumes, growth media or nutrient blends, volumes or feeding frequencies, incubation times, culture vessels, harvesting or filtering methods, etc., may also be used to produce phyto-percolate, and the exemplary method noted above is not intended to exclude other methods of producing phyto-percolate.

As used herein, the term phyto-percolate denotes the composition described above and derivatives thereof. Phyto-percolate also denotes any composition that is made with the process described above or variations to that process that would be recognizable to one of ordinary skill in the art. Applicants reserve the right to more narrowly define the term "phyto-percolate" in the future.

Further, according to various exemplary embodiments of the present invention, the phyto-percolate is isolated into various isolates, such as for example fractions, mixtures of compounds, mixtures of compounds and microorganisms, and/or individual bioactive compounds, by using, for example, the fractionation steps depicted in FIG. 1. Individual bioactive compounds may be isolated from the phyto-percolate or from fractions obtained from the phyto-percolate. Certain exemplary, non-limiting processes are described below.

Referring now to the exemplary flow chart depicted in FIG. 1, phyto-percolate is passaged in series through four chromatography columns having dimensions of 2.7 cm×23 cm (approximately 100 mL of resin at full capacity each) at a flow rate of approximately ~6 mL per minute using a pump such as a peristaltic pump. The rate is selected for optimal binding, and is also based on the flow rate of the slowest resin, ($C_{18}$). The process is optimized to enable the fractionation of approximately 180 L of phyto-percolate. Other variations and modifications of these methods, including an optimization of the process to accommodate other sample volumes, will be apparent to those of ordinary skill in the art.

Following passage of approximately 18 L through a resin, such as a DEAE resin, the column is replaced with a fresh column and the bound material from the prior approximate ~18 L immediately eluted, filtered through a 0.2 µm filter and the eluates stored in sterile containers. Similarly, and according to this exemplary embodiment, the anion and cation exchange resins are replaced after the passage of approximately ~36 L of material through each. A single hydrophobic resin, ($C_{18}$), is used for the entire process. All eluted fractions from the first three columns are immediately run through sterile filters and stored in sterile containers. Elution of the material bound to the $C_{18}$ column requires the use of organic solvents, which are subsequently removed as detailed below. The material that does not bind to any of the four columns, having been depleted of the majority of the organic constituents, is labeled as the "flow-through" fraction and is collected into sterile containers for subsequent testing and use.

A detailed description of each step in the separation process is now described according to one exemplary embodiment of the present invention. First, the chromatography column resins are prepared in accordance to the following process. DEAE Cellulose (a weak anion exchange resin widely used for isolation of proteins) is used in this exemplary process. Prior to use, DEAE cellulose is pretreated with strong base and acid solution to strip off any contaminants that might interfere with the binding of proteins or contaminate the proteins thus isolated. Approximately twenty grams of DEAE-cellulose are rehydrated in approximately ~300 mL of water (ultrapure water is used in this exemplary embodiment) and allowed to swell overnight or an equivalent time at room temperature in a 1 L flask. Water is decanted from the settled/packed resin and the resin is resuspended in an additional ~300 mL of water such as ultrapure water. This resuspension and decanting procedure is repeated two more times through the course of approximately twenty-four hours. The washed resin is resuspended in ~200 ml of 0.1 M NaOH/0.5 M NaCl then transferred to a 600 ml Buchner funnel according to this exemplary embodiment. The flask is then rinsed with an additional approximate 50 ml of 0.1 M NaOH/0.5 M NaCl, and the material suspended in the rinse is also transferred to the funnel. The resin is allowed to sit in this solution for ~10 minutes before the solution is allowed to flow through by gravity. The resin is then rinsed with an additional ~750 ml of 0.1M NaOH/0.5 M NaCl. This filtering procedure is then repeated using 0.5 M NaCl and again using 0.1 M HCl/0.5 M NaCl. The resin is initially rinsed with ~2 L water such as ultrapure water followed by a further rinsing with ~5 L of ultrapure water until the pH of the effluent is greater than five. The DEAE-cellulose slurry is then transferred to five columns (according to this exemplary embodiment, the five columns measuring 2.7 cm×23 cm) and allowed to settle. The packed columns have bed volumes of ~100 ml and are stored at 4° C. until use in this exemplary embodiment.

Further, according to this exemplary embodiment, approximately 100 g of a dry resin such as BioRad AG 1-X8 Strong Base Anion Exchange Resin, (catalogue number 140-1441, received in chloride form, 100-200 dry mesh, 106-180 μm wet bead diameter, quaternary ammonium functionality), is used. To remove any unwanted oxidation contaminants, the resin is exhausted by first hydrating it with deionized water and then loading the beads into a glass column equipped with a glass filter at the bottom of each column. By passing approximately 500 mL of 1.0 M sodium chloride solution through the resin over a period of about three hours, the resin swells and releases any unwanted oxidation products. This process also converts the resin to a chloride ion (Cl) form. After this salt treatment, the resin is rinsed with approximately 2 L of deionized water to remove excess sodium chloride.

The anion exchange resin, now completely in the chloride (Cl) form, is converted into the hydroxide (OH) form by passing approximately 500 mL of 2.0 M sodium hydroxide solution through the column over a period of about 2 hours. The resin is subsequently rinsed with approximately 7.0 L of deionized water, overnight, using a gravity siphon drip as the effluent may be slightly off-color and have an ammonia-like odor. Following this step, the resin's effluent is clear, colorless, and odorless, for this exemplary embodiment. The solution eluting from the column is pH neutral as measured with indicating strips. This anion exchange resin is now considered to be regenerated and ready for use.

Further, according to this exemplary embodiment, approximately 100 g of a dry resin such as DOWEX MONOSPHER® 88 Strong Acid Cation Exchange Resin, (400-700 μm bead diameter with sulfonate functionality, available from Dow Chemical, Midland, Mich.), is used. As for the anion exchange resin, unwanted oxidation contaminants are exhausted by first hydrating with deionized water and then loading the beads into a glass column equipped with a glass filter at the bottom of each column. Passage of approximately 500 mL of 1.0 M sodium chloride solution through the resin over a period of about 3 hours releases any unwanted oxidation products and removes any ions that may have been on the resin from production. The sodium chloride exhaustion causes the resin to convert completely to the sodium ($Na^+$) form. After this salt treatment, the resin is rinsed with approximately 2.0 L deionized water to remove excess sodium chloride.

The cation exchange resin, now completely in the sodium ($Na^+$) form, is converted to the acid ($H^+$) form by passing approximately 500 mL of 2.0 M hydrochloric acid solution through the column over a period of about two hours. The resin is subsequently rinsed with ca. 3.0 L of deionized water, until the solution eluting from the column is pH neutral as measured with indicating strips. This cation exchange resin is now considered to be regenerated and ready for service.

Further, and in accordance with this exemplary embodiment, at the silica gel 90 $C_{18}$-reversed phase column ($C_{18}$), approximately 25 g of resin is resuspended in ultrapure water, packed into a column, and washed with approximately 5 volumes of water prior to use.

Continuing on with the description of this exemplary embodiment, the following paragraphs provide a detailed timetable for the fractionation process. The phyto-percolate is pumped through columns set up in sequence such that the effluent from one column flows through to the next column, at a flow rate of approximately 6.9 ml/min. Additionally, collection vessels are cleaned and dried for flow-through collection. The saved flow-through is passaged through a 0.2 μm filter system and is stored at approximately 4-25° C.

After the first ~18 L passes through, the DEAE-cellulose column is removed and eluted with 250 ml 1M NaCl, pH 8.3. The eluate is filtered through a 0.2 μm filter, labeled and stored at 4° C. Then, a fresh DEAE-cellulose column is placed into the fractionation system and the process resumed. After another ~18 L are passaged, the DEAE-cellulose, anion exchange, and cation exchange columns are removed and each eluted with approximately 250 ml 1M NaCl, pH 8.3. The eluates are passaged through individual 0.2 μm filter systems, labeled and stored at approximately 4° C.

According to this exemplary embodiment, fresh DEAE-cellulose, anion exchange and cation exchange columns were placed into the fractionation system and the process resumed. After another ~18 L, the DEAE-cellulose column is removed and eluted with 250 ml NaCl, pH 8.3. The eluate is passaged through a 0.2 μm filter system, labeled and stored at 4° C. Elution of material bound to the $C_{18}$ column (from all material): The $C_{18}$ column is drained of excess water and purged with compressed nitrogen to remove residual water.

The column is then flushed with approximately 50 mL of acetone to remove the last traces of water and organics, followed by approximately 50 mL of ethyl acetate and finally approximately 50 mL of hexanes. The solution is then dried with excess, anhydrous, magnesium sulfate, and filtered through glass wool or another similar material.

The solvent is then removed with a stream of nitrogen, and then reconstituted with approximately 5 mL of ethyl acetate and transferred to a glass vial of known mass. The solvent is removed with nitrogen and the final mass is taken.

Further, the DEAE-cellulose, anion exchange, and cation exchange columns were each eluted with approximately 250 ml 1M NaCl, pH 8.3. The eluates were passed through individual 0.2 μm filter systems, labeled and stored at approximately 4° C. 1 mL of eluate from the cation exchange column (labeled as "Fraction 3" or "F3" in FIGS. 2-9 and described herein) is the eluate captured from the cation exchange columns after the phyto-percolate has passed through the first three columns using the methods described above, and is approximately 160 fold concentrated compared to the unseparated phyto-percolate introduced into the separation process. That is, for every 160 mL of phyto-percolate introduced into the process, 1 mL of eluate was isolated in PF3.

Fraction 4 labeled as F4 in FIGS. 2-9 and described herein, is the flow-through captured at the end of the fractionation series after the phyto-percolate has passed through all 4 columns in accordance with the exemplary methods described above.

In the experiments for which results are presented in FIGS. 2-9, the dilutions provided are those of the completed, unseparated phyto-percolate composition or of the specific fractions identified. For example, since the total volume of flow-through isolated in F4 is identical to that of the unfractionated phyto-percolate, the relative concentration(s) of all constituents in F4 was identical to that of the unseparated phyto-percolate, whereas the relative concentration of constituents in a 1:20 dilution of the F3 fraction eluted from the strong cation exchange resin is approximately 8 fold concentrated relative to unseparated phyto-percolate (since 1 mL of F3 is obtained for every 160 mL of phyto-percolate, a 1:20 dilution equates to the constituents therein being approximately 8 fold concentrated relative to unseparated phyto-percolate).

According to this exemplary embodiment, phyto-percolate and the flow-through/F4 were tested as they appeared in their original concentrations right off the columns, only diluted 1:20 and 1:100 as described herein. The culture of peripheral blood mononuclear cells ("PBMC") is prepared from two vials of frozen PBMCs that were obtained from normal healthy human subjects by a commercial vendor, and were added to 2×10 ml medium and centrifuged. PBMCs were resuspended and cultured in RPMI1640/5% FBS for 24 h. (1 vial of frozen cells in 11 ml medium).

Treatment agents for this exemplary method comprise three agents: unseparated phyto-percolate ('PAZ'), fraction 3 ('F3'), fraction 4 ('F4'). Treatment concentration for each was 1:20 and 1:100. An exemplary sample preparation method for each agent by dilution is as follows: First, a 1:10 dilution is prepared by combining 0.7 ml agent (PAZ, F3, or F4)+6.3 ml RPMI1640/5% FBS to obtain a total volume of 7 ml of a 1:10 solution. Second, a 1:50 dilution is prepared by combining 1.2 ml of the 1:10 dilution of each respective agent with 4.8 ml RPMI1640/5% FBS for a total volume of 6 ml of 1:50 solution. In addition, for diluted fraction 3 (F3), 1M NaOH was used to adjust pH to 7.0.

According to this exemplary embodiment, seeding, treatment, and detection are accomplished by the following steps. Two dishes of PBMCs were combined and the small amount of PBMCs was stained with 0.4% Trypan blue and the cell number of PBMCs was counted using known techniques.

In this embodiment, an enzyme linked immune-sorbent assay ("ELISA") analysis of inflammatory cytokine secretion, (a protocol provided in a commercial kit for the parallel quantification of the production of human cytokines), was employed. The PBMC were first seeded into a twenty-four well plate (337,600 cells/each well in 320 μl medium) and incubated at 37° C. for 48 hours. In this exemplary embodiment, an additional 320 μl of culture medium was added, and cells were cultured for 48 hours. For the control cultures, the 320 μl of additional medium contained no additional components. To stimulate the production of several cytokines, parallel cultures of PBMC were treated with 50 ng/ml phorbol myristate acetate ('PMA') and 1 μg/ml ionomycin for 24 hours, followed by addition of 0.64 μl PMA/0.64 μl ionomycin and incubation for an additional twenty-four hours. For cultures in which PBMC were treated with phyto-percolate or fractions derived therefrom, the 320 μl of additional medium which contained 1:10 or 1:50 dilutions of phyto-percolate or fractions 3 or 4 derived therefrom (to yield final dilutions in the cultures of 1:20 or 1:100) was added just before incubation for 24 hours, and then incubated with or without PMA+ionomycin treatment for an additional 24 hours. Duplicate PBMC cultures were examined for each of these conditions. At the end of the incubation period, the cultures were centrifuged and the supernatant medium was collected and aliquots stored at −70° C. The quantity of cytokines present in each of the culture medium samples was subsequently determined using a Multi-Analyte ELISArray Kit (product number MEH-004A) for human inflammatory cytokines and methods provided by SA Biosciences.

Analysis of the effect of phyto-percolate or fractions isolated therefrom on the DNA-binding activity of NF-κB in the nuclear protein fractions of the cultured PBMC was determined as follows in this exemplary embodiment: approximately 18.26 mL of suspended PBMC were added to approximately 18 mL of culture medium and 2 mL of this cell suspension (2,718,000 cells in 2 mL) were seeded into each 60 mm culture dish. In this exemplary embodiment, additional 2 mL of culture medium was added. For the control cultures, the 2 mL of additional medium contained no additional components. Culture of cells stimulated with TNF-α was performed identically, including addition of 2 mL of additional medium at the start of the culture, but 2 μL of TNF-α (50 ng/ml) was added to these cultures one hour before harvesting. For cultures in which PBMC were treated with phyto-percolate or fractions derived therefrom, the 2 mL of additional medium contained 1:10 or 1:50 dilutions of phyto-percolate or fractions 3 or 4 derived therefrom (to yield final dilutions in the cultures of 1:20 or 1:100) was added just before incubation. Two positive controls for the inhibition of the DNA binding activity of NF-κB were performed. In one case, PBMC were cultured for 24 h in the presence of 25 μM G2535 for 24 h followed by TNF-α treatment for 1 h. In the second case, PBMC were cultured for 24 h in the presence of 25 μM Genistein for 24 h followed by TNF-α treatment for 1 h. Duplicate PBMC cultures were examined for each of these conditions which were then cultured at 37° C. for 24 h before harvesting.

At the end of the incubation period, nuclear proteins were extracted from the cells according to the method of set forth in PubMed-Cancer Research 65:6934, 2005 and electrophoretic mobility shift assays ("EMSA") were performed for the binding of NF-κB to a synthetic radiolabeled DNA sequence corresponding to the cognate NF-κB DNA-binding element using an established protocol such as the one set forth in PubMed-Cancer Research 65:6934, 2005.

With reference now to FIGS. 2-9, the methods of effecting various cytokines and NF-κB, with the phyto-percolate, which is denoted by the phrase "PAZ", and fractions thereof, are discussed according to certain exemplary embodiments of the present invention. Although specific examples of the composition effecting the production of various cytokines and the DNA-binding activity of NF-κB are discussed herein, the disclosure is not limited to only those examples or the compositions and quantities, dilutions, or fractions of the compositions discussed herein, although Applicants reserve the right to claim certain quantities, dilutions, or fractions at a later date. As will be discussed in more detail below, additional fractions and even compounds may be isolated from the phyto-percolate.

Figure 2A:
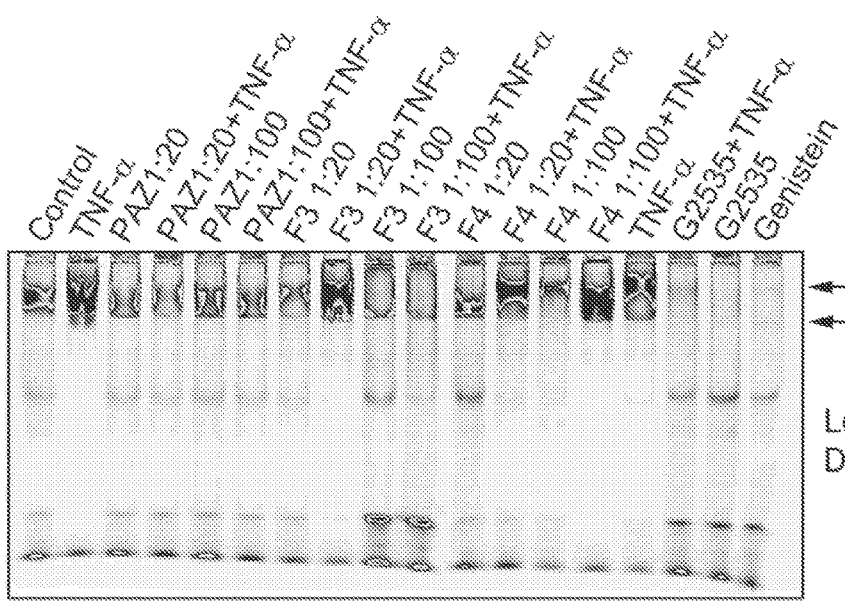
Figure 2B:
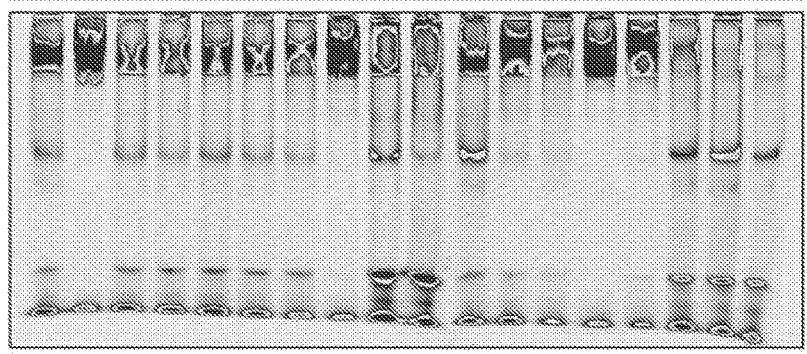

With reference now to FIGS. 2A-2D, raw data is shown from various electrophoretic mobility shift assays ("EMSA") for NF-κB, performed using a deoxyoligonucleotide corresponding to the DNA sequence to which NF-κB binds, labeled with an infrared dye. Specifically, FIGS. 2A and 2B depict both results in "low density" in which the bands were visualized using an infrared scanner (Li-Cor Corporation) for a short period of time (FIG. 2A), and in "high density" in which image obtained from the same gel was enhanced (FIG. 2B). FIGS. 2C and 2D depict the results when the tests resulting in the assays shown in FIGS. 2A and 2B were re-run for a longer time period (3 hours compared to 2 hours) using an identical amount of the nuclear protein.

Figure 3:
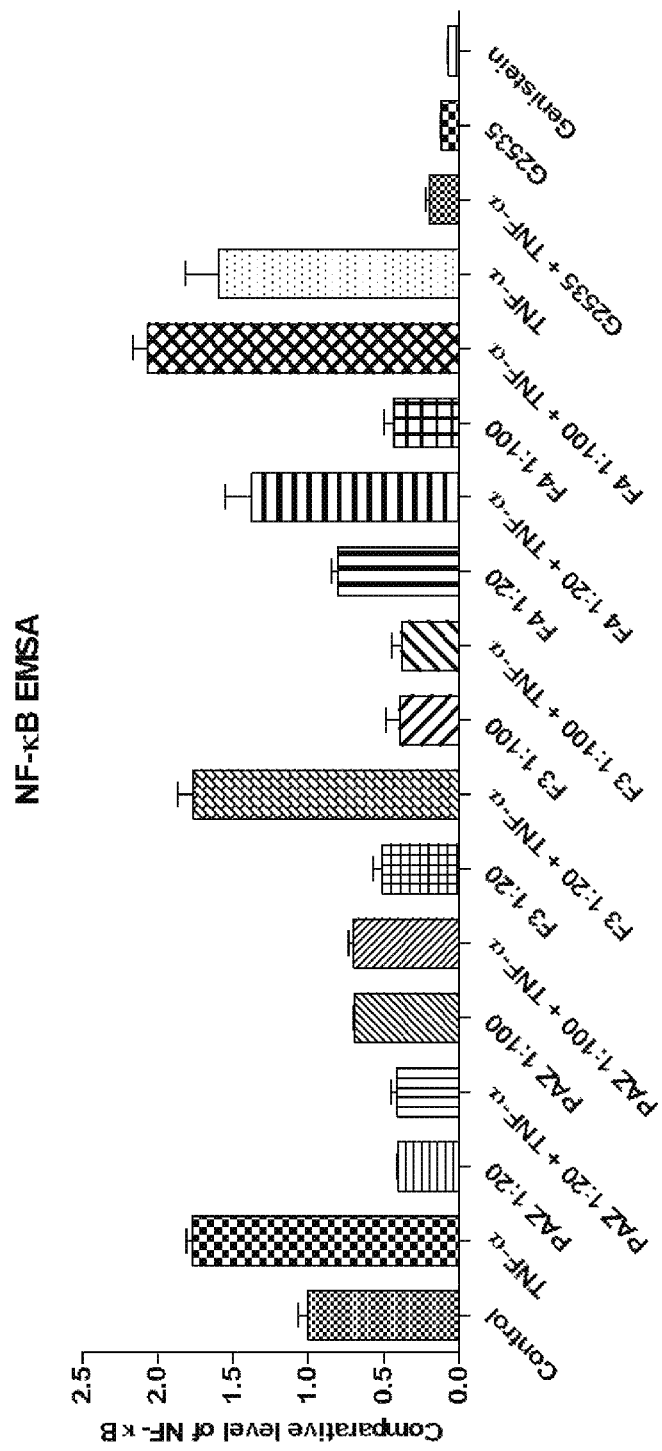
FIG. 3 shows a bar graph illustrating the quantitative analysis of the results obtained in the experiment presented in FIGS. 2A-2D, thus illustrating the efficacy of the method effecting NF-κB according to various exemplary embodiments of the present invention.

Turning now to FIG. 3, the effects of administering phyto-percolate, as well as various fractions that were obtained by chromatographic treatment of the complete phyto-percolate composition, on the DNA-binding activity of NF-κB in PBMC, with or without stimulation with phrobol myristate acetate (PMA), are shown according to certain exemplary embodiments of the present invention. Active NF-κB is a dimeric protein that binds to a cognate DNA sequence to control the transcription of specific proteins that play key roles in inflammation. Therefore, the more NF-κB expressed and binding to DNA, the greater the amount of inflammatory proteins that will be produced, and the greater the inflammatory response. Reducing the overall amount of NF-κB that binds to DNA sequence of NF-κB target genes lowers inflammation as well as reduces the other effects of NF-κB such as reducing the activation of various viruses such as the HIV virus.

As shown in FIG. 3, control, unstimulated and untreated PBMC were tested to determine the native amount of NF-κB that binds to a radiolabeled DNA probe. This represents a baseline measurement of NF-κB activity that is expressed as a relative unit of 1.0. According to this example, when tumor necrosis factor alpha or TNF-α was added, the DNA-binding activity of NF-κB was significantly increased to a relative level of almost 2.0. However, when a composition comprised of 1:20 dilution of phyto-percolate (labeled 'PAZ') was added to the PBMC, the concentration of NF-κB decreased significantly, compared to the control, to a relative level of approximately 0.4 units. As shown in FIG. 3, and according to various exemplary embodiments of the present invention, phyto-percolate in a 1:20 and 1:100 dilution when combined with TNF-α, phyto-percolate in a 1:100 dilution alone, fractions 3 and 4 (labeled "F3" and "F4") alone in a 1:20 and 1:100 dilution, and fraction 3 in a 1:100 dilution in the presence of TNF-α, reduced the overall concentration of NF-κB compared to the control, whereas fraction 4 in 1:100 dilutions plus TNF-α increased NF-κB concentration. FIG. 3 also shows the results of adding TNF-α, G2535 plus TNF-α, G2535 alone, and genistein alone. As shown in FIG. 3, phyto-percolate alone, fraction 3 and fraction 4 inhibited NF-κB, and both phyto-percolate and fraction 3 inhibited TNF-α induced activation of NF-κB.

Therefore, administering phyto-percolate may decrease the DNA-binding activity of NF-κB, which in turn reduces inflammation. Further, since NF-κB activation promotes the replication and/or function of certain viruses, such as the HIV virus, reducing the total DNA-binding activity of NF-κB may reduce or prevent the pathological effects of certain viruses, such as HIV. The present invention contemplates that any therapeutic effects from a reduced DNA-binding activity of NF-κB, now known or discovered in the future, can be achieved by administering an effective amount of phyto-percolate, and the dilutions, fractions, compounds and derivatives thereof.

Figure 4:
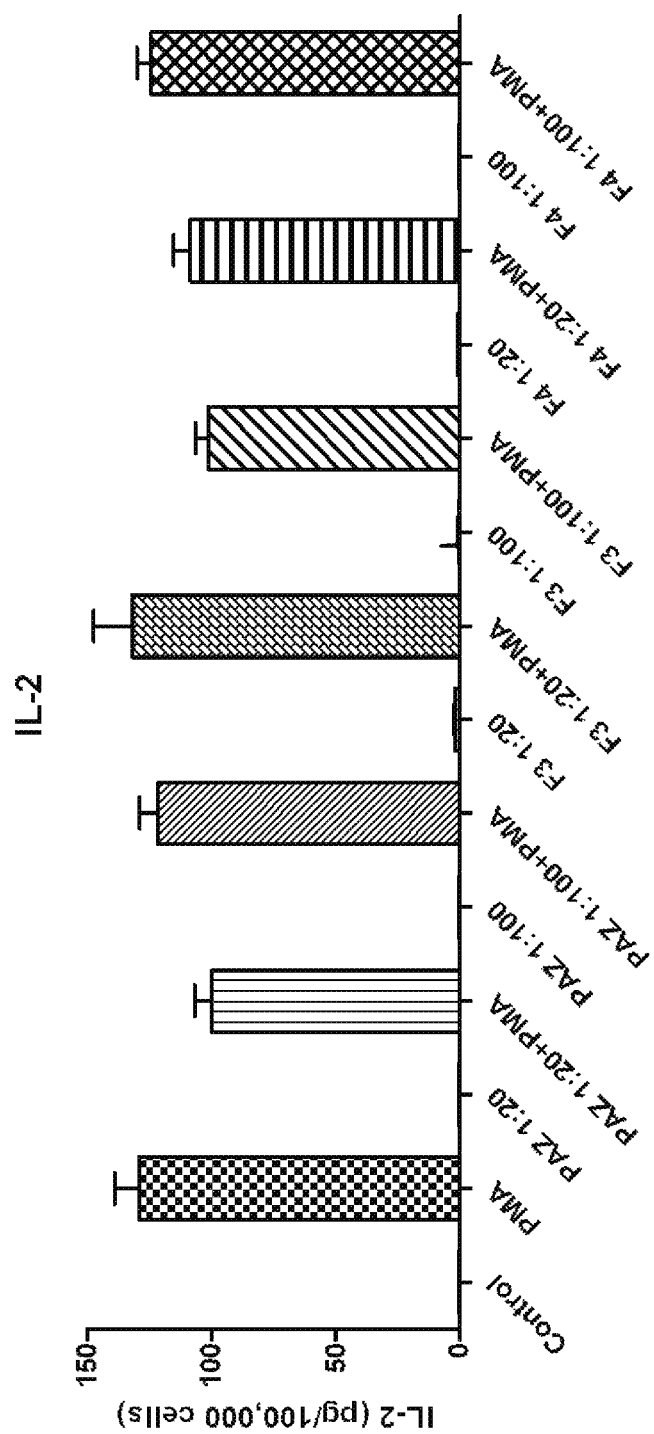
FIG. 4 shows a bar graph illustrating the efficacy of the method on the production of the cytokine IL-2 according to various exemplary embodiments of the present invention.
Figure 5:
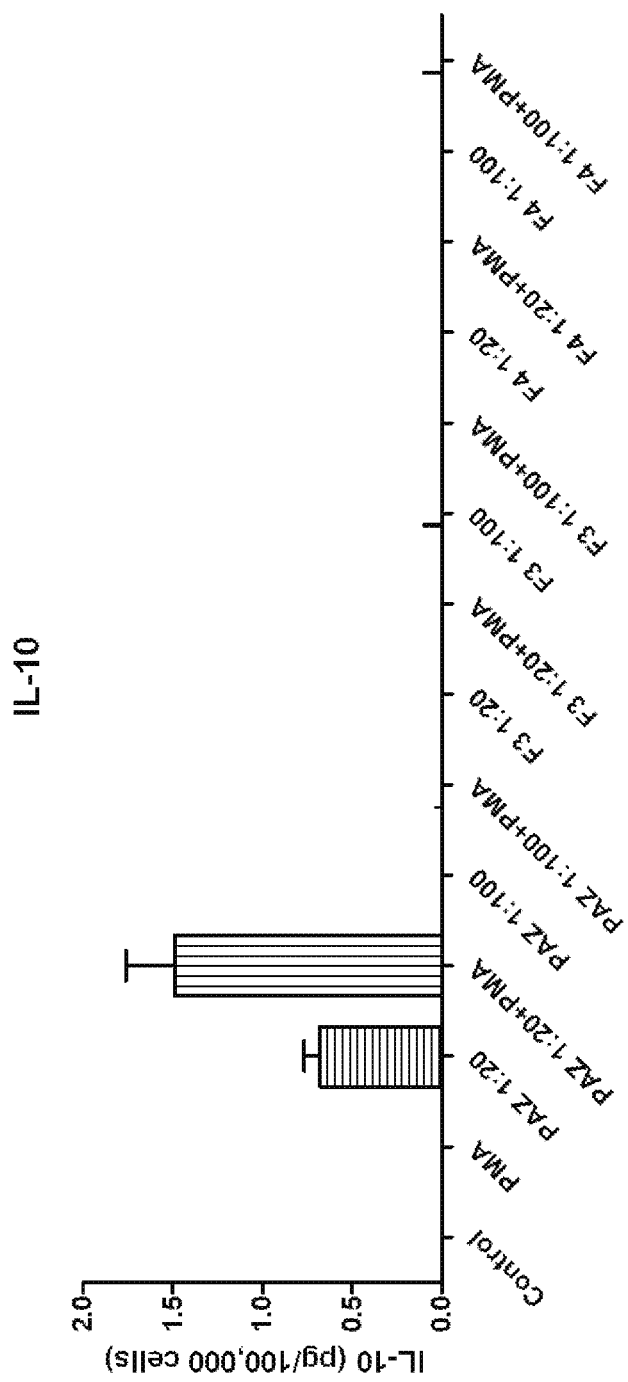
FIG. 5 shows a bar graph illustrating the efficacy of the method on the production of the cytokine IL-10 according to various exemplary embodiments of the present invention.
Figure 6:
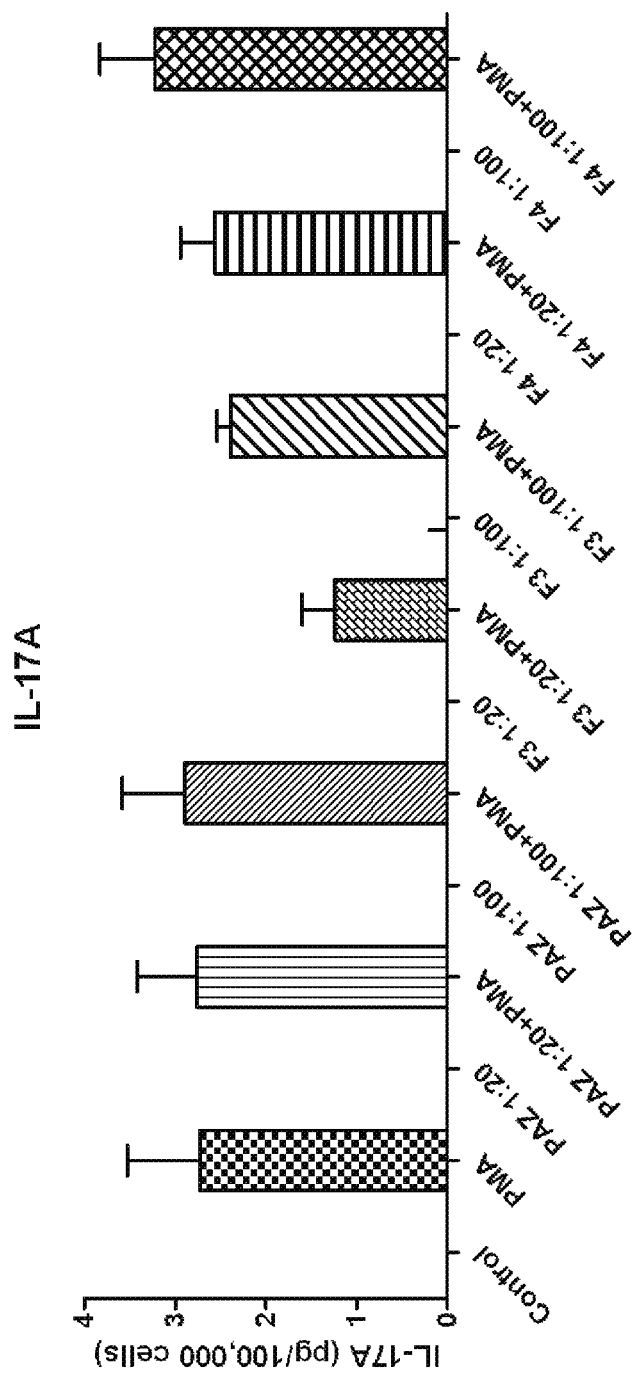
FIG. 6 shows a bar graph illustrating the efficacy of the method on the production of the cytokine IL-17A according to various exemplary embodiments of the present invention.

Turning now to FIGS. 4-6 and in accordance with various exemplary embodiments of the present invention, the effect of phyto-percolate on the production by PBMC of various interleukins is discussed. While certain specific interleukins such as IL-10 and IL-17A are discussed, phyto-percolate also has effects on other interleukins and in other inflammatory pathways.

With particular reference now to FIG. 4, the quantity of IL-2 produced (expressed as pg of IL-2/100,000 cells) was measured following the addition of phyto-percolate and various dilutions and fractions thereof to PBMC in the absence of other stimulants, or when added to PBMC treated with PMA, according to one exemplary embodiment of the present invention. As shown, a control consisting of untreated cultured PBMC did not secrete a detectable quantity of IL-2 into the culture medium, whereas additions of PMA to the cultured PBMC resulted in secretion of approximately 125 pg/100,000 cells IL-2. Treatment of cultured PBMC with 1:20 or 1:100 phyto-percolate dilutions did not induce production of detectable quantities of IL-2 (i.e. approximately the same results as for control, untreated PBMC). The addition of a 1:20 dilution of phyto-percolate, fraction 3 in a 1:100 dilution, and fraction 4 in a 1:20 dilution to PBMC stimulated with PMA reduced the production of IL-2 compared to PBMC treated with PMA alone. Treatment of cultured PBMC with fraction 3 and fraction 4, derived from chromatographic fractionation of phyto-percolate, at 1:20 and 1:100 dilutions did not induce production of detectable quantities of IL-2, similar to the control. However, according to this exemplary embodiment, when phyto-percolate in a 1:100 dilution and fraction 3 of phyto-percolate in a 1:20 dilution and fraction 4 of phyto-percolate a 1:100 were tested on PBMC in the presence of PMA, the overall amount of IL-2 did not change significantly when compared with the addition of PMA alone.

Therefore, as depicted in this exemplary embodiment, the addition of phyto-percolate and dilutions, fractions or derivatives thereof may reduce the concentration of IL-2 produced by PBMC in response to agents that stimulate IL-2 production, but they neither do not stimulate the production of IL-2 themselves, nor do they potentiate the production of IL-2 by agents known to induce production of this cytokine (for example PMA). The action of phyto-percolate to reduce (or not to increase) the production of IL-2 by PBMC reflects its ability to reduce the amount of inflammation as well as other effects of IL-2 now known or discovered in the future. According to various exemplary embodiments of the present invention, the ability to not up-regulate an inflammatory cytokine such as IL-2 while simultaneously up-regulating an anti-inflammatory cytokine such as IL-10 is effective at reducing the amount of inflammation and is superior to conventionally available therapies as it reduces undesirable side effects.

Turning now to FIG. 5 and in accordance with yet another exemplary embodiment of the present invention, FIG. 5 depicts the overall production and secretion of IL-10 (expressed as pg of IL-10/100,000 cells) when phyto-percolate, various fractions and dilutions thereof, and PMA are added to cultured PBMC. As shown in FIG. 5, the phyto-percolate in a 1:20 dilution alone and in a 1:20 dilution tested in conjunction with PMA increased the overall secretion of IL-10 compared to control PBMC, which did not show secretion of detectable quantities of IL-10 into the medium. In this one exemplary embodiment as shown, the various other dilutions and fractions of phyto-percolate, alone or in combination with PMA, did not appear to effect the overall concentration of IL-10. However, as in the cases with the other exemplary embodiments depicted herein, fractions 3 and 4 comprise only a small percentage of the composition of phyto-percolate and this result does not limit the invention to the point where phyto-percolate in the concentrations and fractions that did not increase IL-10 concentration necessarily will not ever increase IL-10 concentration in the future.

Therefore, phyto-percolate may increase the overall concentration of IL-10. Increasing the overall concentration of IL-10 should reduce the amount of inflammation as IL-10 is an anti-inflammatory cytokine. Further, the present invention contemplates that the other effects now known or discovered in the future that are attributable to IL-10 can be achieved by the addition of phyto-percolate.

According to various exemplary embodiments of the present invention, phyto-percolate's effects to reduce inflammation can occur due to its effect of reducing the DNA-binding activity of NF-κB, alone or in combination with increasing the production and secretion of anti-inflammatory cytokines such as IL-10 and by reducing inflammatory cytokines such as IL-2 or tumor necrosis factor-alpha ("TNF-α") as noted below. Therefore, the present invention contemplates that phyto-percolate has effects on multiple different cytokines at one time to achieve an overall effect, such as reducing inflammation according to various exemplary embodiments.

With reference now to FIG. 6, and in accordance with one exemplary embodiment of the present invention, the addition of phyto-percolate to a mixture of cultured PBMC to effect the overall production and secretion of IL-17A (expressed as pg of IL-17 secreted/100,000 cells) is disclosed. Besides IL-17A, interleukin 17 (synonymous with interleukin 17A) is similarly affected by the addition of phyto-percolate. As shown, unstimulated cultured control PBMC do not secrete detectable levels of IL-17A whereas the addition of PMA to cultured PBMC resulted in a significant increase of IL-17A to approximately 3 pg/100,000 cells. The addition of phyto-percolate in a 1:20 dilution or a 1:100 dilution did not result in detectable secretion of IL-17A from control PBMC, and the addition of 1:20 dilution or a 1:100 dilution of phyto-percolate or fraction 4 in a 1:100 dilution in the presence of PMA did not cause any change in the levels of IL-17A secreted in response to PMA alone. Fraction 3 and fraction 4 of phyto-percolate in both 1:20 dilution and 1:100 dilution did not result in detectable secretion of IL-17A from control PBMC. An addition of fraction 3 of phyto-percolate in a 1:20 dilution significantly reduced the secretion of IL-17A by PBMC in response to PMA treatment to approximately 1 pg/100,000 cells. Fraction 3 of phyto-percolate in a 1:100 dilution as well as fraction 4 of phyto-percolate in a 1:20 dilution also reduced the section of IL-17A by PBMC in response to PMA treatment as shown.

Figure 7:
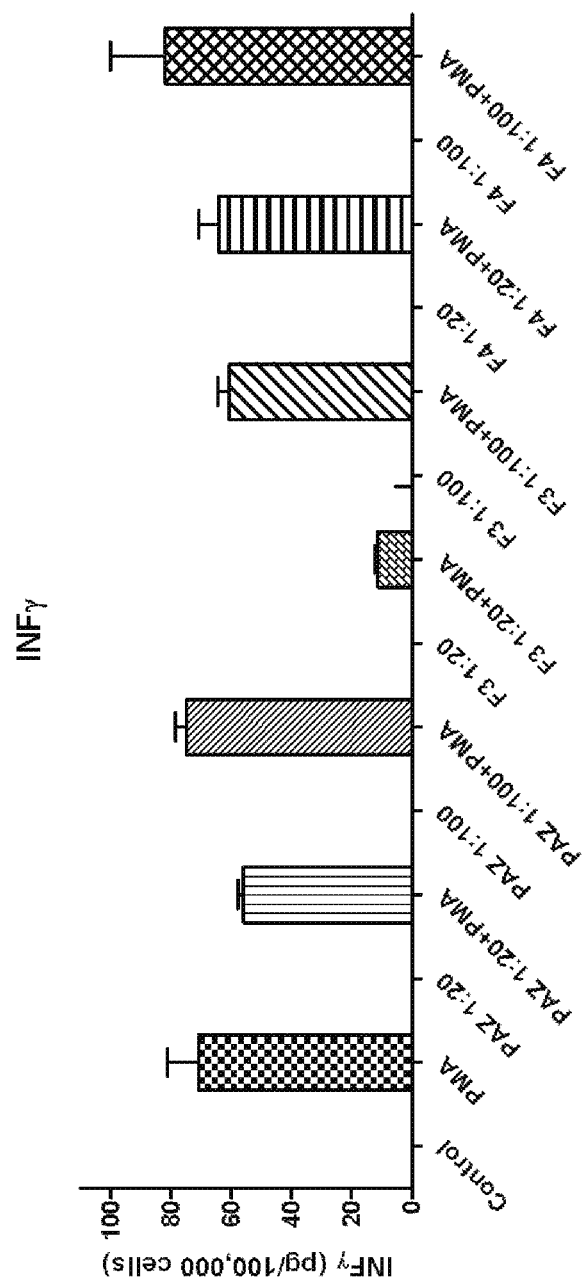
FIG. 7 shows a bar graph illustrating the efficacy of the method on the production of the cytokine INF-γ according to various exemplary embodiments of the present invention.
Figure 8:
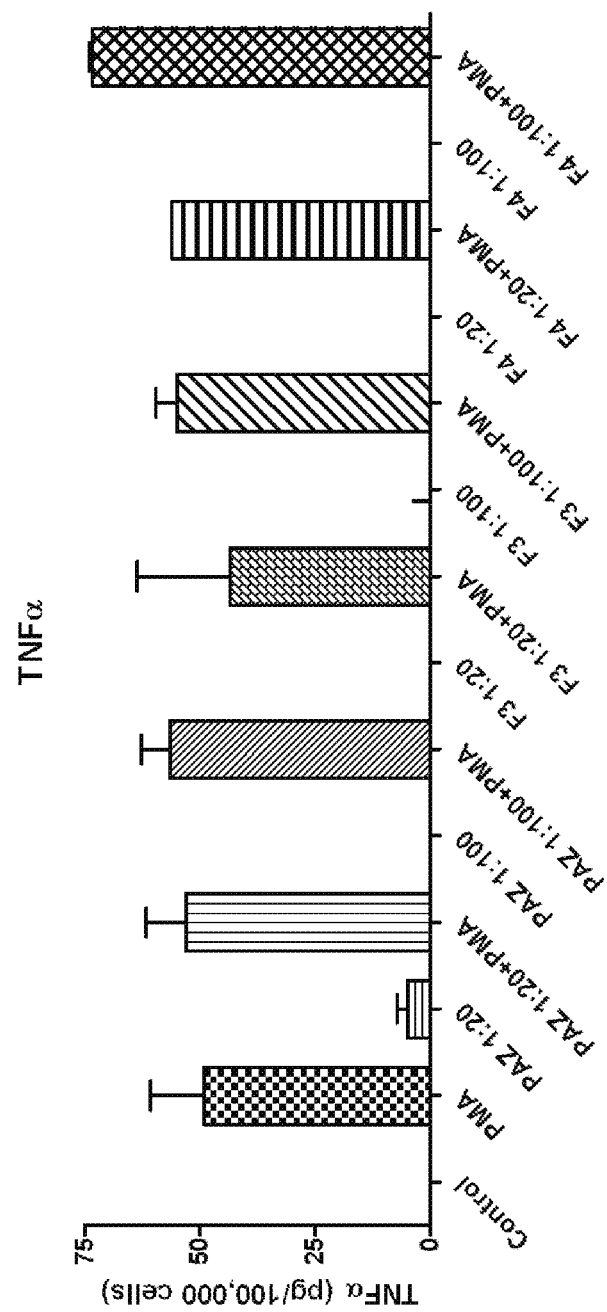
FIG. 8 shows a bar graph illustrating the efficacy of the method on the production of the cytokine TNF-α according to various exemplary embodiments of the present invention.
Figure 9:
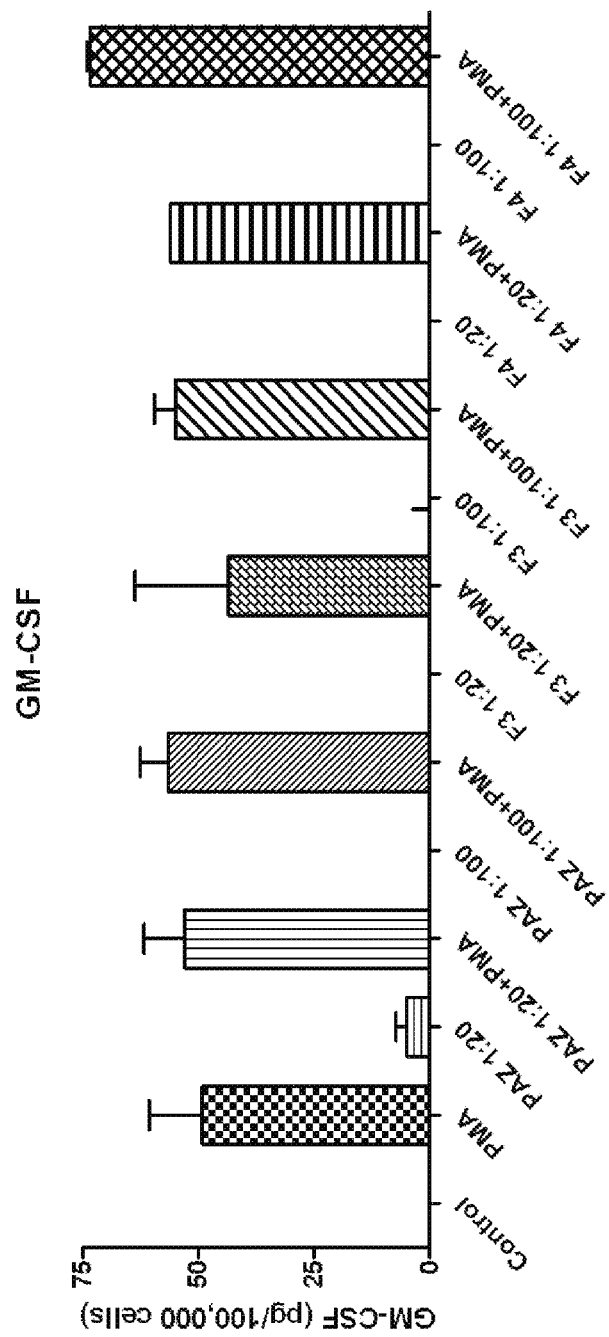
FIG. 9 shows a bar graph illustrating the efficacy of the method on the production of GM-CSF according to various exemplary embodiments of the present invention.

FIGS. 7-9 show the effect of phyto-percolate on other cytokines. Specifically, the effect of phyto-percolate in various dilutions and fractions on interferon-gamma (IFN-γ), tumor necrosis factor-alpha (TNF-α), and granulocyte macrophage colony stimulating factor (GM-CSF) is disclosed.

As shown now in FIG. 7, and in accordance with one exemplary embodiment of the present invention, the effect of phyto-percolate on the concentration of IFN-γ (expressed as pg of IFN-γ secreted/100,000 cells) is disclosed. According to this exemplary embodiment, unstimulated cultured control PBMC do not secrete detectable levels of IFN-γ, whereas the addition of PMA to cultured PBMC resulted in significant secretion of IFN-γ to approximately 70 pg/100,000 cells. While the addition of phyto-percolate to cultured PBMC in a dilution of 1:20, a dilution of 1:100, or fraction 3 or fraction 4 in these dilutions did not result in the secretion of detectable levels of IFN-γ in this exemplary embodiment, the addition of phyto-percolate in a dilution of 1:20 to PBMC, in combination with PMA, decreased the overall secretion of IFN-γ that is induced by PMA alone. The addition of fraction 3 in 1:20 dilution significantly decreased the PMA-induced secretion of IFN-γ, to approximately 10 pg/100,000 cells. Fraction 3 in a 1:100 dilution decreased the PMA-induced secretion of IFN-γ to approximately 60 pg/100,000 cells, as did fraction 4 in 1:20 dilution.

Therefore, phyto-percolate does not induce the production of IFN-γ and may modulate the overall production of IFN-γ caused by other agents, thus enabling the benefits that may be derived therefrom.

With reference now to FIG. 8 and in accordance with an exemplary embodiment of the present invention, effect of phyto-percolate on the production and secretion of TNF-α (expressed as pg secreted/100,000 cells) was measured. According to this exemplary embodiment, unstimulated cultured control PBMC do not secrete detectable levels of TNF-α whereas the addition of PMA to cultured PBMC resulted in significant secretion of TNF-α of approximately 50 pg/100,000 cells. The phyto-percolate in a 1:100 dilution, or fraction 3 in a 1:20 or 1:100 dilution, or fraction 4 of phyto-percolate in a 1:20 or 1:100 dilution, do not induce the secretion of detectable levels of TNF-α. Phyto-percolate and fractions derived therefrom did not significantly alter the PMA-induced secretion of TNF-α by cultured PBMC.

Turning now to FIG. 9 and in accordance with another exemplary embodiment of the present invention, the effect of administering various concentrations and fractions of phyto-percolate on the production and secretion of GM-CSF by PBMC (expressed as pg secreted/100,000 cells) is discussed. As shown, a control consisting of unstimulated cultured PBMC did not produce a measurable amount of GM-CSF, whereas the addition of PMA induced secretion of approximately 50 pg/100,000 cells. Phyto-percolate in a 1:20 dilution induced the secretion of a very low level GM-CSF (approximately 5 pg/100,000 cells) whereas a 1:100 dilution of phyto-percolate, or various dilutions of fractions 3 and 4, did not induce GM-CSF secretion. Further, phyto-percolate, as well as fraction 3 in both a 1:20 dilution and a 1:100 dilution, and fraction 4 at 1:20 dilution, did not influence the production of GM-CSF by PBMC in the presence of PMA.

Therefore, according to these exemplary embodiments, phyto-percolate by itself in various dilutions, and fractions therefrom do not cause the secretion of appreciable quantities of GM-CSF, and phyto-percolate in various dilutions, and fractions therefrom do not significantly alter the production of GM-CSF that is induced as the result of treatment by other agents.

Therefore, according to various exemplary embodiments of the present invention, the administration of phyto-percolate regulates various cytokines and NF-κB to achieve certain desired effects such as the reduction of inflammation. Unlike compositions of the prior art, phyto-percolate can regulate multiple cytokines to achieve reduced inflammation. For example, as shown and discussed above, the administration of phyto-percolate can up-regulate IL-10 without up-regulating IL-2, to more greatly reduce inflammation.

Further, phyto-percolate and various dilutions and fractions thereof are capable of inhibiting NF-κB and TNF-α induced activation of NF-κB, thus indicating that phyto-percolate functions as an antioxidant. Also, according to certain exemplary embodiments, administering phyto-percolate in various dilutions and fractions, especially fraction 3, significantly inhibits the DNA-binding activity of NF-κB. Administering an effective amount of phyto-percolate will not induce certain pro-inflammatory cytokines such as TNF-α or IFN-γ, while inducing various anti-inflammatory cytokines such as IL-10, to reduce inflammation. Further, according to the various exemplary embodiments herein, the administration of phyto-percolate did not have a toxic or irritant effect on cells or tissue.

In various embodiments, isolates derived from the phyto-percolate or from fractions thereof, can be used to affect cytokine levels in cells exposed to pathogens or pathogenic substances. In exemplary embodiments discussed herein below, "Compounds 20-25," "GC," (also referred to herein as gelding culture, gelding reserve, GR, or GL) and "DC," (also referred to herein in some bar graphs as "80×") are isolated and tested in methods similar to the testing of the phyto-percolate and fractions F3 and F4 discussed above, to show their individualized effects on various cytokines in bovine, canine and human immune responses. In no way does the term "compound" imply that the designated isolate is a pure molecule. Instead, "compound" herein means an "isolate," which may comprise a single chemical species, a complicated mixture of substances, or even a complex mixture of bioactive substances and microorganisms. An isolate herein may comprise a culture or a supernatant of a culture, such as for example, comprising a mixture of substances in a fluidic medium. Isolates may share one or more common components.

Compounds 20-25, GC and DC were obtained from PAZ using variations of the process depicted by the flowchart of FIG. 1, or separation methods known to one skilled in the art in general. Amongst other physical properties, Compounds 20-25 and GC have similar LC-MS traces, in that each sample shows two major components identified by their LC retention times of 3.29 minutes and 3.64 minutes. The mass spectrometry data corresponding to these components are 453 and 679 Dalton, respectively (M+H). Additionally, the $^{31}$P-NMR spectra for each of the eight isolates were devoid of peaks. Some of the properties of the isolates are summarized in TABLE 1 below:

TABLE 1

Bioactive isolates derived from phyto-percolate

| Cmd. | Source | LC retention times (min) | MS (M + H; Daltons) | $^{31}$P-NMR |
|---|---|---|---|---|
| 20 | ABC Composite Lot #8 PAZ | 3.29; 3.64 | 453; 679 | No peaks |
| 21 | Gelding Reserve PAZ | 3.29; 3.64 | 453; 679 | No peaks |
| 22 | Gelding Reserve PAZ | 3.29; 3.64 | 453; 679 | No peaks |
| 23 | ABC Composite Lot #8 PAZ | 3.29; 3.64 | 453; 679 | No peaks |
| 24 | Gelding Reserve | 3.29; 3.64 | 453; 679 | No peaks |
| 25 | Gelding Reserve | 3.29; 3.64 | 453; 679 | No peaks |
| GC | Gelding reserve tank sample | 3.29; 3.64 | 453; 679 | No peaks |
| DC | Dilute ABC Composite Lot #8 PAZ | 0.58; 2.43; 2.93; 3.14; 3.50; 3.78; 4.07; 4.35; 4.92; 5.14; 5.57; 6.99; 7.35; 7.63 | n/a | No peaks |

As indicated in TABLE 1, the component with the 3.29 minute LC retention time has a mass (M+H) of 453 Dalton while the component with the 3.64 minute LC retention time has a mass (M+H) of 679 Dalton. An ion at 475 Dalton is attributed to an M+Na, i.e. the molecule associated with a sodium ion, which is common phenomenon in electrospray ionization.

As indicated in TABLE 1, the isolate referred to as "DC" (or "80×") shows a more complicated component profile than the other isolates. Approximately fourteen (14) components are revealed on LC-MS, and it is believed that two of these (3.14 and 3.50 minute retention times) correlate with the two major components found in the other isolates. Thus in various embodiments, isolates may comprise major components identified by having one or more of the LC retention times set out in TABLE 1. In various embodiments, isolates may comprise two major components, one identified by having an LC retention time of about 3.14 to 3.30 minutes, and the other identified by having an LC retention time of about 3.50 to 3.70 minutes.

Regulation of TNF-α, Lactoferrin, IFN-γ, IL-1β, Serum Amyloid-A (SAA), IL-6 and β-Defensin in Bovine Epithelial Cells Exposed to Pathogens or Pathogenic Triggers:

In bovine mastitis, an efficient and rapid, but not overwhelming, immune response is appropriate and necessary to eradicate infection in the animal. However, prolonged elevation of various immune markers, such as TNF-α, lactoferrin, IFN-γ, IL-1β, serum amyloid-A (SAA) and IL-6 can result in harm to tissue, leading to severe losses in milk production and potentially chronic cases of infection. One issue with continued increases in these and other cytokines is that mammary epithelial cells will undergo extensive apoptosis. Continued elevation of immune markers is similar to what is seen when a cow is dried off during mammary gland involution, which can end up causing reduced milk production and subsequently a susceptibility to chronic cases of infection. On the other hand, β-defensin is an antimicrobial peptide that may aid in the eradication of infection in the animal. With these intricacies in mind, a study using bovine cells showed how isolates from phyto-percolate and fractions thereof can be used to regulate production of TNF-α, lactoferrin, IFN-γ, IL-1β, serum amyloid-A (SAA), IL-6 and β-defensin in bovine cells exposed to pathogens or other immune response triggers.

Additionally, isolates from phyto-percolate and fractions thereof may promote antimicrobial responses at sites of infection, such as, for example, in bovine tissue infected with live pathogens, e.g. *Staphylococcus, Streptococcus, Mycoplasma*, and the like, with isolates promoting migration of leucocytes and monocytes to the site of infection, promoting propagation of neutrophils and/or tightening cell junctures to block proteins excreted by the invasive pathogens.

In various embodiments, primary bovine mammary epithelial cells (pBMEC) were treated with Compounds 20, 21, 22, 23, 24, 25, GC, or DC under various conditions, with and without a pathogen or pathogenic substance present, to study the effect the isolates have on the levels of TNF-α, lactoferrin, IFN-γ, IL-1β, serum amyloid-A (SAA), IL-6 and β-defensin. According to various exemplary embodiments of the present invention, administration of Compounds 20-25, GC, or DC regulate various cytokines to various degrees, in order to achieve certain desired effects, such as the reduction of inflammation in bovine mastitis.

Of the cytokines measured in this study, TNF-α and IFN-γ were already discussed above in the tests of phyto-percolate and the F3 and F4 fractions. Lactoferrin, IL-1β, serum amyloid-A (SAA), IL-6 and β-defensin were not discussed previously. Therefore, they are discussed herein below since they are included in the bovine mastitis study involving pBMEC.

Lactoferrin is a globular glycoprotein belonging to the family of transferrin proteins, present in milk amongst other animal secretory fluids. Lactoferrin takes part in an immune response to inflammation, where at acidic pH it sequesters iron to make the elemental nutrient less available to the proliferating bacteria. Lactoferrin also functions as an antibacterial by binding to the lipopolysaccharide of bacterial walls, changing membrane permeability and ultimately destroying the cell. However, lactoferrin can, in some instances, result in bacteria becoming more invasive within the parenchymal tissue. Furthermore, some bacteria have adapted to living in high lactoferrin environments and lactoferrin is even believed to feed bacteria in some instances. In various embodiments, select compounds from phyto-percolate reduce the production and/or secretion of lactoferrin by the pBMEC cells in the presence of pathogenic substances.

IL-1β is a specific interleukin, also known as catabolin. As discussed above, the interleukins form a large group of cytokine proteins. IL-1β is a member of the interleukin-1 family of cytokines, and it is pro-inflammatory and it contributes to inflammatory pain hypersensitivity. In various embodiments, select compounds from phyto-percolate reduce the production and/or secretion of IL-1β by the pBMEC cells in the presence of pathogenic substances.

Serum amyloid-A (or "SAA") is an apolipoprotein secreted in various isoforms at various phases of inflammation. For example, acute-SAAs are secreted during the acute phase of inflammation. The presence of SAA in milk is an indicator of subclinical mastitis, and in general, relatively miniscule inflammatory stimuli can lead to an SAA response. In various embodiments, select compounds from phyto-percolate reduce the production and/or secretion of SAA by the pBMEC cells in the presence of various pathogens or pathogenic substances.

IL-6 is an interleukin is a pro-inflammatory cytokine. IL-6 is elevated in animals and humans having inflammation and various disease states, and it is a diagnostic marker for bovine mastitis and a prediction marker for bovine subclinical mastitis. Generally, decreased IL-6 levels are desired, as the longer the levels are elevated the worse an infection can get due to damage to the epithelium. In various embodiments, select compounds from phyto-percolate reduce the production of IL-6 by the pBMEC cells stimulated with various pathogenic substances.

β-Defensin is a cationic (cysteine and arginine rich) antimicrobial peptide, small in molecular weight compared to the proteins discussed above. Bacterial infections induce expression of bactericidal factors such as β-defensin. For example, *Escherichia coli* trigger an increased expression of β-defensin contributing to the cow's immune defense in bovine mastitis. β-defensin is anti-inflammatory and in some cases (humans, for example) limits the production of pro-inflammatory cytokines. Therefore, increased levels of β-defensin are generally desirable. In various embodiments, select compounds from phyto-percolate increase the production of β-defensin by the pBMEC cells stimulated with various pathogenic substances.

For the in vitro bovine mastitis tests, pBMEC were cultured in a collagen gel matrix for 8 days to allow sufficient time for cell growth. For testing, the cell cultures were treated with lipoteichoic acid (LTA) derived from *Staphylococcus aureus*, lipopolysaccharides (LPS) derived from *Escherichia coli*, or a mastitis strain of *Streptococcus uberis* (herein "Strep. uberis"), either alone (as a control response to the stimulant) or in combination with one of the isolates, namely Compounds 20-25, GC or DC, with subsequent analysis of the levels of TNF-α, lactoferrin, IFN-γ, IL-1β, serum amyloid-A (SAA), IL-6 or β-defensin as appropriate for the particular test at hand. For some tests, the naturally occurring flavone genistein is used for comparison. As in the tests above using phyto-percolate and its fractions, the protein of interest in a particular test was quantified through the use of a bovine ELISA reagent kit specific for the detection of the particular bovine target.

In general, tests used Compounds 20, 21, 22, 23, 24, 25, GC or DC in liquid form as isolated, (i.e. supernatant or infusion or liquid fraction). The volume percent (vol %) of an isolate used in a test protocol was 20% based on the final volume of the media. The cells were plated in 24-well culture plates, with 500 μL total per well. Therefore, 100 μL of each compound was used to achieve the desired 20 vol % of the test compound. When *Strep. uberis* was used as the pathogen, it was used at a concentration of $1 \times 10^7$ cfu/mL. After the pBMEC was treated for 24 hours with LPS, LTA, or *Strep. uberis* alone or in combination with Compound 20-25, GC or DC, the supernatant was harvested and analyzed for TNF-α, lactoferrin, IFN-γ, IL-1β, serum amyloid-A (SAA), IL-6 or β-defensin using the appropriate bovine ELISA kit. Each set of experiments relating to a particular cytokine are discussed below.

Figure 10:
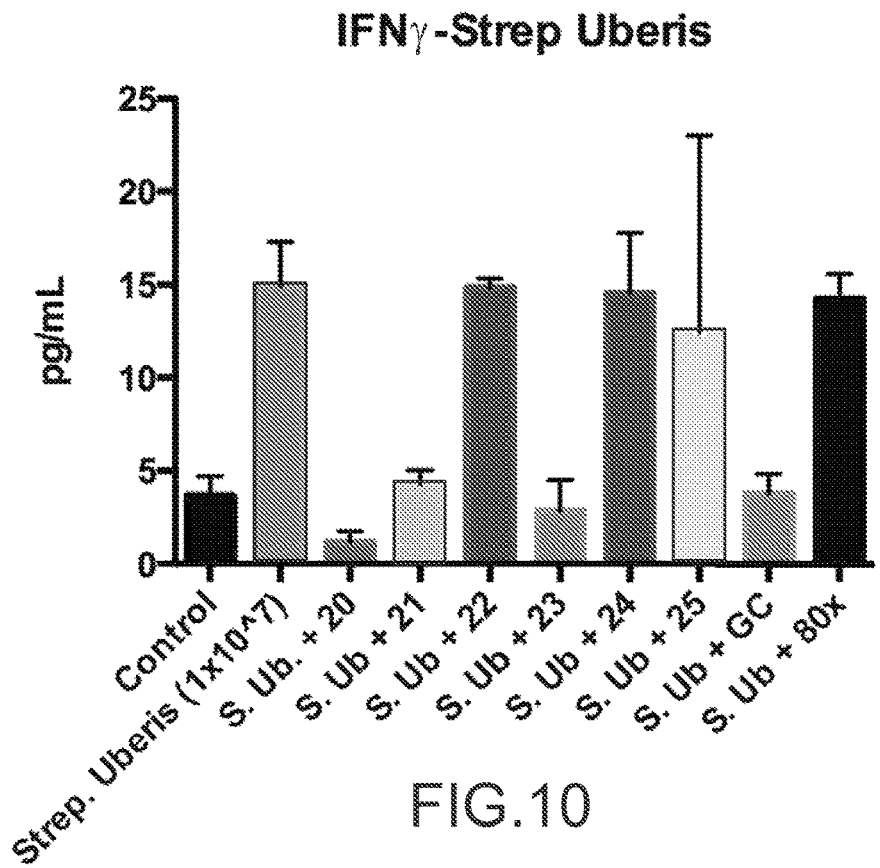
FIG. 10 shows a bar graph illustrating the efficacy of the method on the production of IFN-γ in the presence of *Streptococcus uberis* according to various exemplary embodiments of the present invention.
Figure 11:
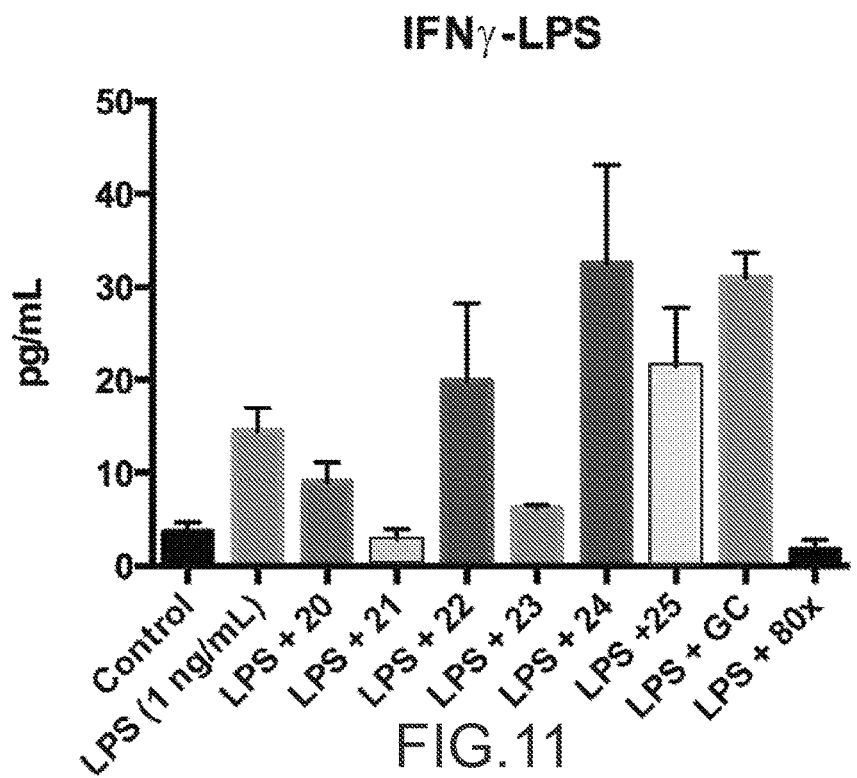
FIG. 11 shows a bar graph illustrating the efficacy of the method on the production of IFN-γ in the presence of LPS according to various exemplary embodiments of the present invention.
Figure 12:
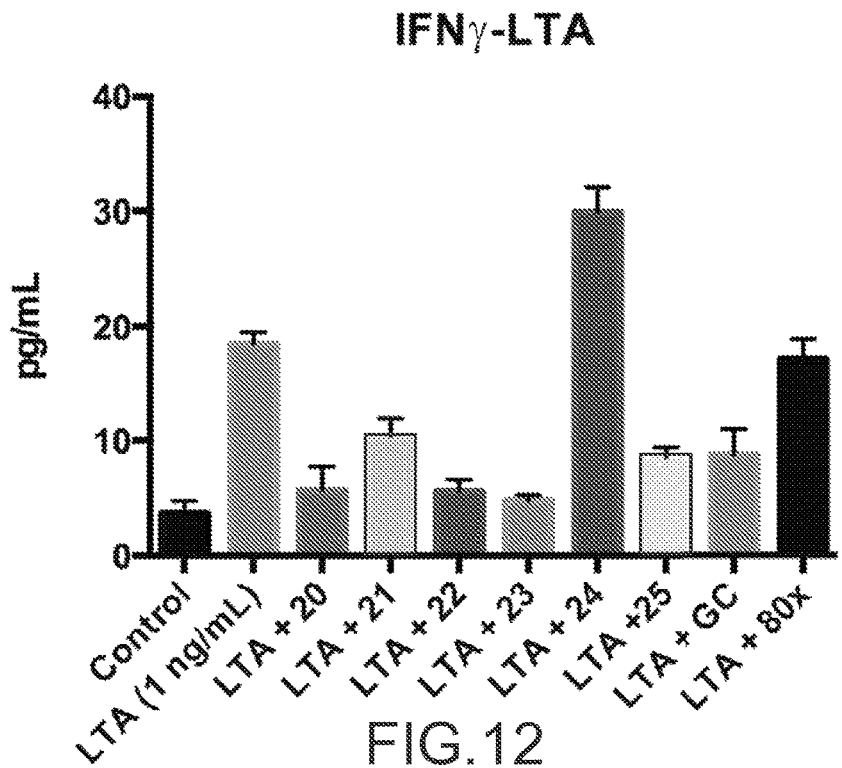
FIG. 12 shows a bar graph illustrating the efficacy of the method on the production of IFN-γ in the presence of LTA according to various exemplary embodiments of the present invention.

Referring now to FIGS. 10-12, IFN-γ secretion from the pBMEC was determined for each of Compounds 20-25, GC and DC ("80×" in the figures) in the presence of *strep. uberis* (FIG. 10), LPS (FIG. 11) or LTA (FIG. 12). As evident from the bar graphs in FIGS. 10-12, *Strep. uberis*, LPS and LTA induced IFN-γ secretion by the pBMEC as expected. *Strep. uberis* had increased effects on IFN-γ secretion compared to LTA and LPS, with LTA resulting in higher IFN-γ secretion than LPS. Compounds 21, 23 and GC resulted in decreased IFN-γ secretion in combination with *strep. uberis*, while Compounds 22, 24, 25, and DC had no effects. Compound 24 in combination with LTA increased IFN-γ secretion, DC did not appear to change the IFN-γ secretion induced by LTA only, and all other compounds decreased IFN-γ secretion. Compound 24 and GC stimulated IFN-γ secretion when cells were subjected to LPS. Compounds 22 and 25 did not appear to change the IFN-γ secretion induced by LPS alone, and all the other compounds suppressed IFN-γ secretion. Therefore, in various embodiments, select compounds derived from phyto-percolate or its fractions can be used to induce or suppress IFN-γ secretion during inflammation, thus enabling the therapeutic benefits that may be derived therefrom. Increased IFN-γ is often associated with cyctotoxic cells that are responsible for removing and killing bacteria. Hence in some instances, elevation of IFN-γ may help with eradication of infection.

Figure 13:
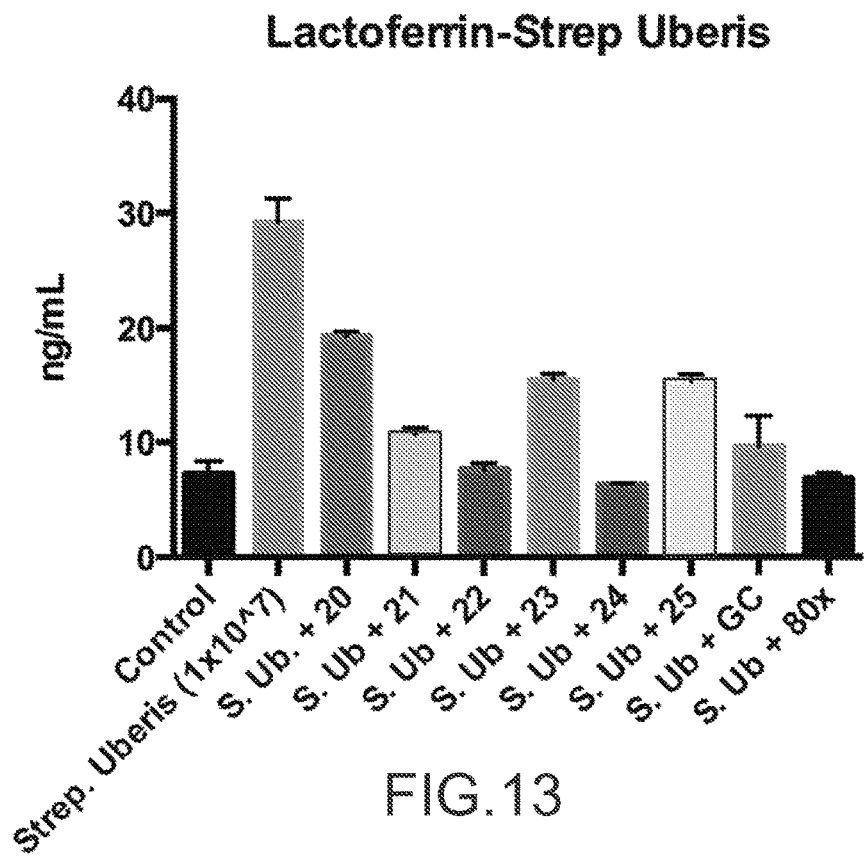
FIG. 13 shows a bar graph illustrating the efficacy of the method on the production of lactoferrin in the presence of *Streptococcus uberis* according to various exemplary embodiments of the present invention.
Figure 14:
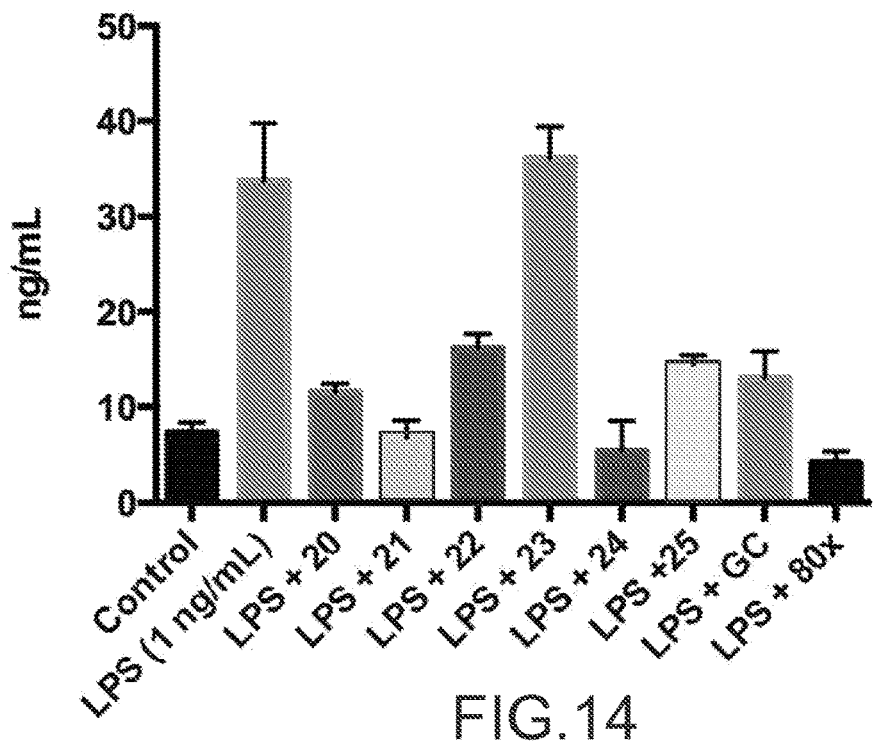
FIG. 14 shows a bar graph illustrating the efficacy of the method on the production of lactoferrin in the presence of LPS according to various exemplary embodiments of the present invention.
Figure 15:
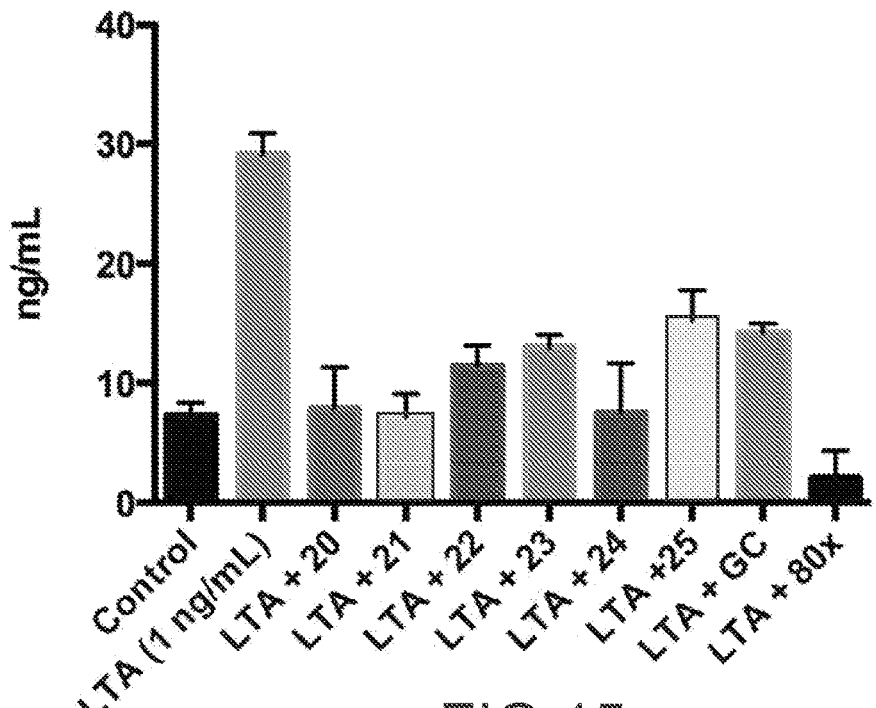
FIG. 15 shows a bar graph illustrating the efficacy of the method on the production of lactoferrin in the presence of LTA according to various exemplary embodiments of the present invention.

Referring now to FIGS. 13-15, lactoferrin secretion from the pBMEC was determined for each of Compounds 20-25 GC and DC ("80×" in the figures) in the presence of *strep. uberis* (FIG. 13), LPS (FIG. 14) or LTA (FIG. 15). As evident from the bar graphs in FIGS. 13-15, *strep. uberis*, LPS and LTA stimulated lactoferrin secretion by the pBMEC as expected. Compounds 21, 24 and DC had the most pronounced decrease in lactoferrin secretion when the lactoferrin secretion was stimulated by LPS. However, all compounds except for Compound 23 resulted in decreased lactoferrin when the pathogenic substance was LPS. Compounds 21, 24, and DC in combination with LTA had the most pronounced decrease in lactoferrin, but all compounds resulted in decreased secreted lactoferrin. Compounds 22, 24, and DC resulted in the largest decrease to lactoferrin when pBMEC was exposed to *strep. uberis*. All compounds did suppress lactoferrin secretion relative to lactoferrin secretion in the presence of *strep. uberis* alone. Therefore, in various embodiments, select compounds derived from phyto-percolate or its fractions can be used to suppress lactoferrin secretion during inflammation, thus enabling the therapeutic benefits that may be derived therefrom.

Figure 16:
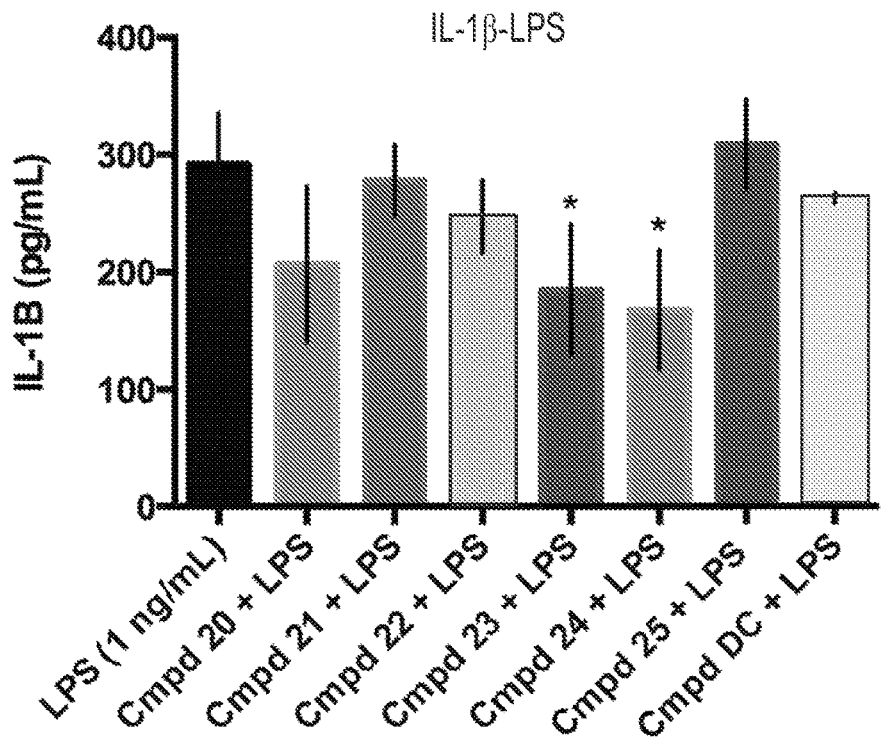
FIG. 16 shows a bar graph illustrating the efficacy of the method on the production of IL-1β in the presence of LPS according to various exemplary embodiments of the present invention.
Figure 17:
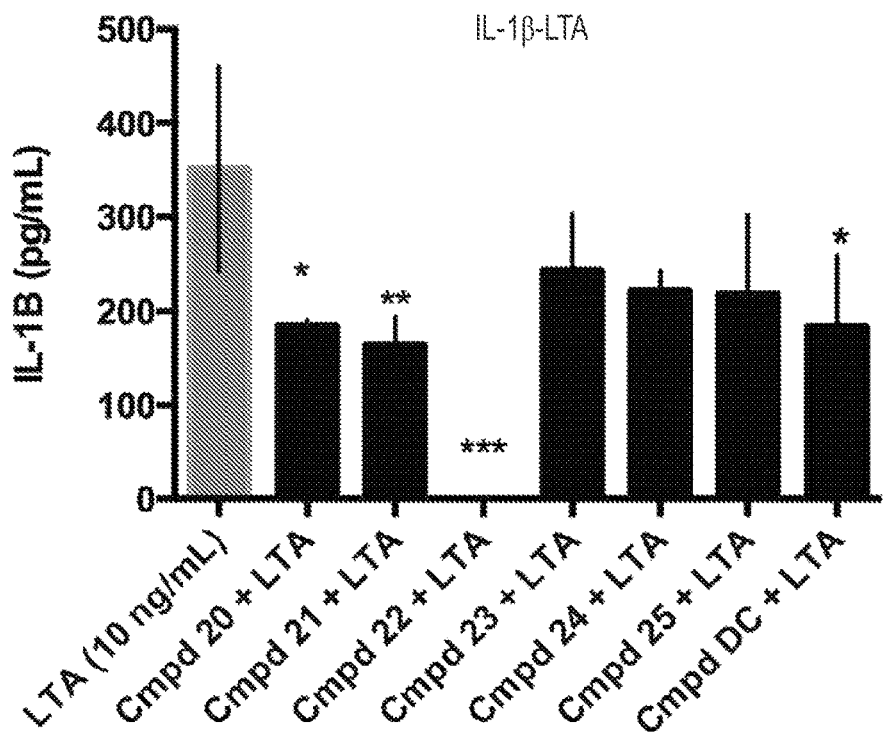
FIG. 17 shows a bar graph illustrating the efficacy of the method on the production of IL-1β in the presence of LTA according to various exemplary embodiments of the present invention.

With reference now to FIGS. 16 and 17, IL-1β secretion from the pBMEC was determined for each of Compounds 20-25 and DC in the presence of LPS (FIG. 16) or LTA (FIG. 17). As evident from the bar graphs in FIGS. 16 and 17, LPS and LTA stimulated IL-1β secretion by the pBMEC. As evident from the bar graphs in FIGS. 16 and 17, Compounds 23 and 24 suppressed IL-1β secretions in pBMEC exposed to LPS relative to pBMEC exposed to LPS alone. Compounds 20, 21, 22 and DC resulted in decreased IL-1β when treated in combination with LTA compared to cells treated with LTA only. LTA is known to be a more significant inducer of IL-1β than LPS. With IL-1β being a pro-inflammatory cytokine, the suppression of IL-1β by selected compounds derived from phyto-percolate or its fractions can be used to modulate IL-1β secretion during inflammation, thus enabling the therapeutic benefits that may be derived therefrom.

Figure 18:
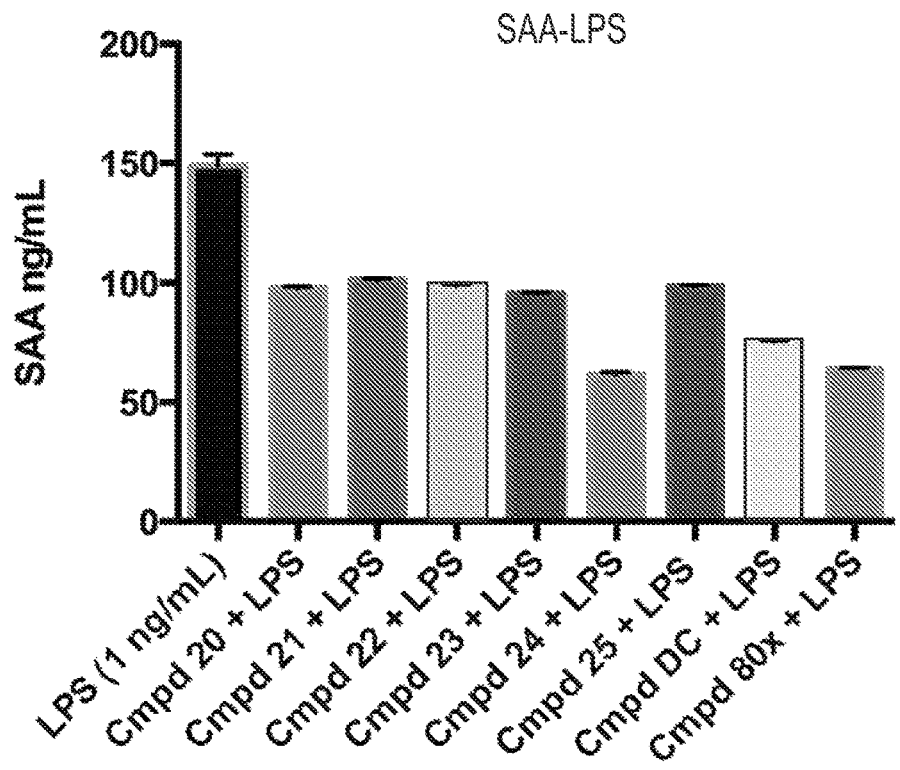
FIG. 18 shows a bar graph illustrating the efficacy of the method on the production of serum amyloid-A (SAA) in the presence of LPS according to various exemplary embodiments of the present invention.
Figure 19:
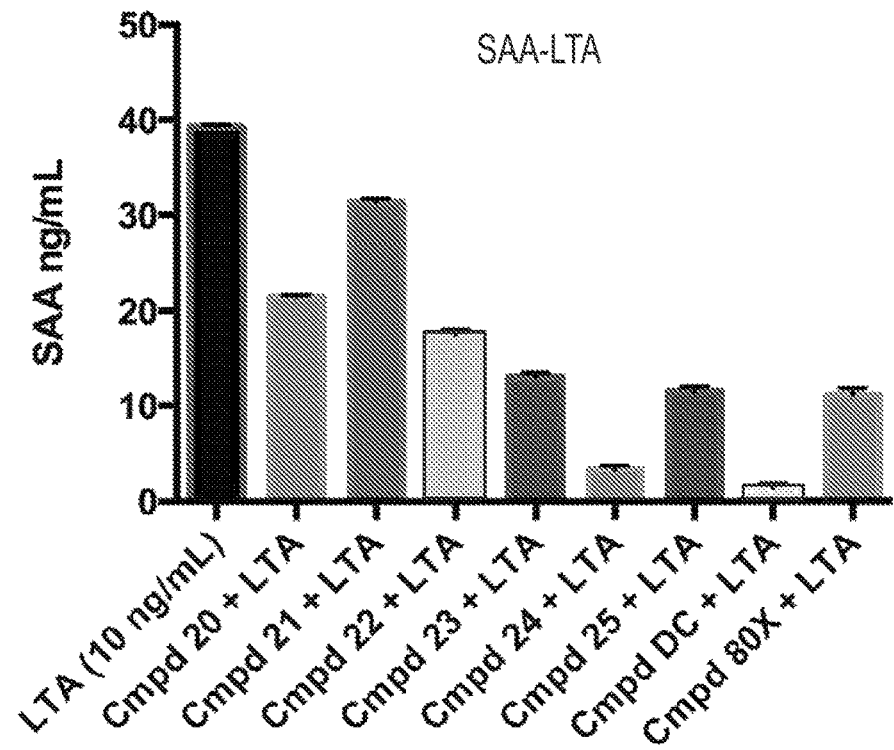
FIG. 19 shows a bar graph illustrating the efficacy of the method on the production of serum amyloid-A (SAA) in the presence of LTA according to various exemplary embodiments of the present invention.

Referring now to FIGS. 18 and 19, serum amyloid-A (SAA) secretion from the pBMEC was determined for each of Compounds 20-25, GC and DC in the presence of LPS (FIG. 18) or LTA (FIG. 19). As evident from the bar graphs in FIGS. 18 and 19, LPS and LTA stimulated SAA secretion by the pBMEC as expected, with LPS stimulating SAA more than LTA. As evident from the bar graphs in FIGS. 18 and 19, Compounds 24 and DC in combination with LTA resulted in the most significant decrease in SAA. All compounds decreased SAA in response to LPS exposure. However, Compound 24 was more effective at SAA suppression. Therefore, in various embodiments, select compounds derived from phyto-percolate or its fractions can be used to suppress SAA during inflammation, thus enabling the therapeutic benefits that may be derived therefrom.

Figure 20:
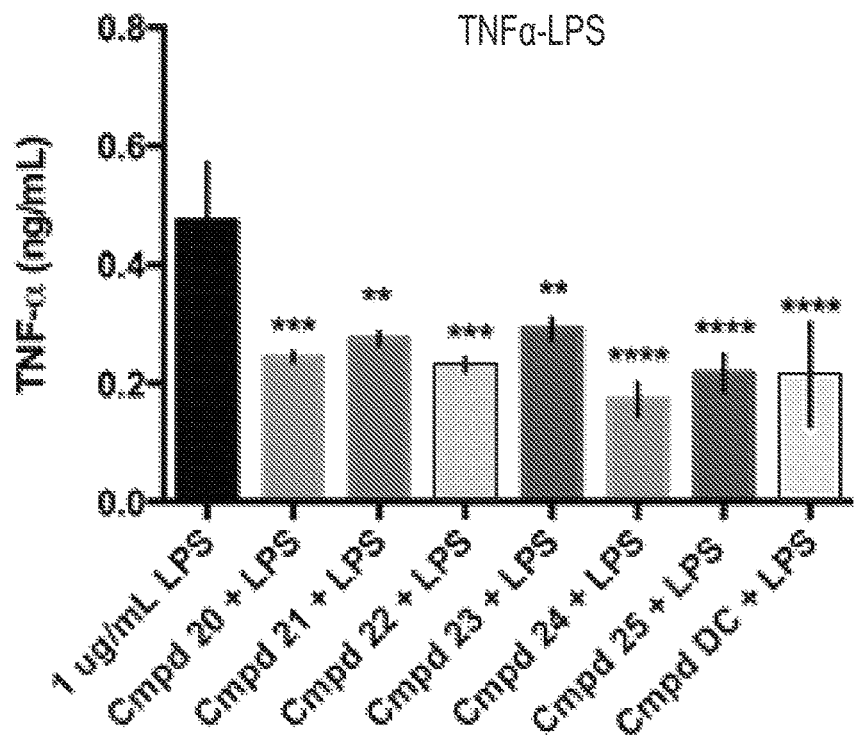
FIG. 20 shows a bar graph illustrating the efficacy of the method on the production of TNF-α in the presence of LPS according to various exemplary embodiments of the present invention.

With reference now to FIG. 20, the effect of Compounds 20-25 and DC on the production and secretion of tumor necrosis factor-α (TNF-α) from pBMEC was measured for cells exposed to LPS. As evident in FIG. 20, LPS resulted in stimulation of TNF-α. Compound 24 resulted in the most significant decrease in TNF-α (63.4% decrease in this case) compared to the other compounds when the pBMEC was exposed to LPS. In regards to TNF-α, continually elevated levels can actually lead to coliform mastitis, which present persistent issues with infection. Thus suppression of TNF-α may be advantageous in certain cases of mastitis. In various embodiments, select compounds derived from phyto-percolate or its fractions can be used to suppress TNF-α during inflammation, thus enabling the therapeutic benefits that may be derived therefrom.

Figure 21:
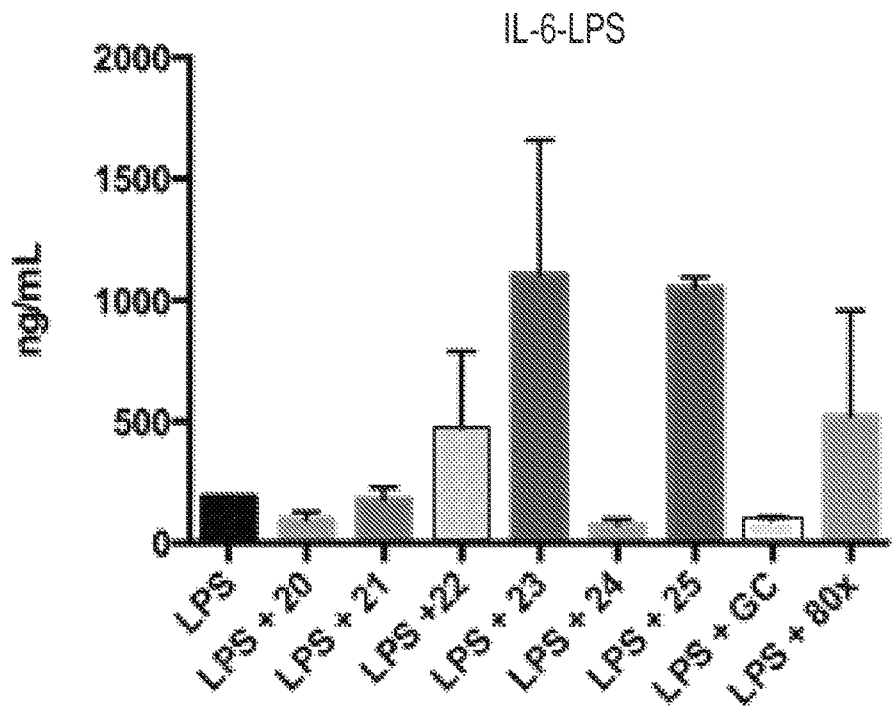
FIG. 21 shows a bar graph illustrating the efficacy of the method on the production of IL-6 in the presence of LPS according to various exemplary embodiments of the present invention.
Figure 22:
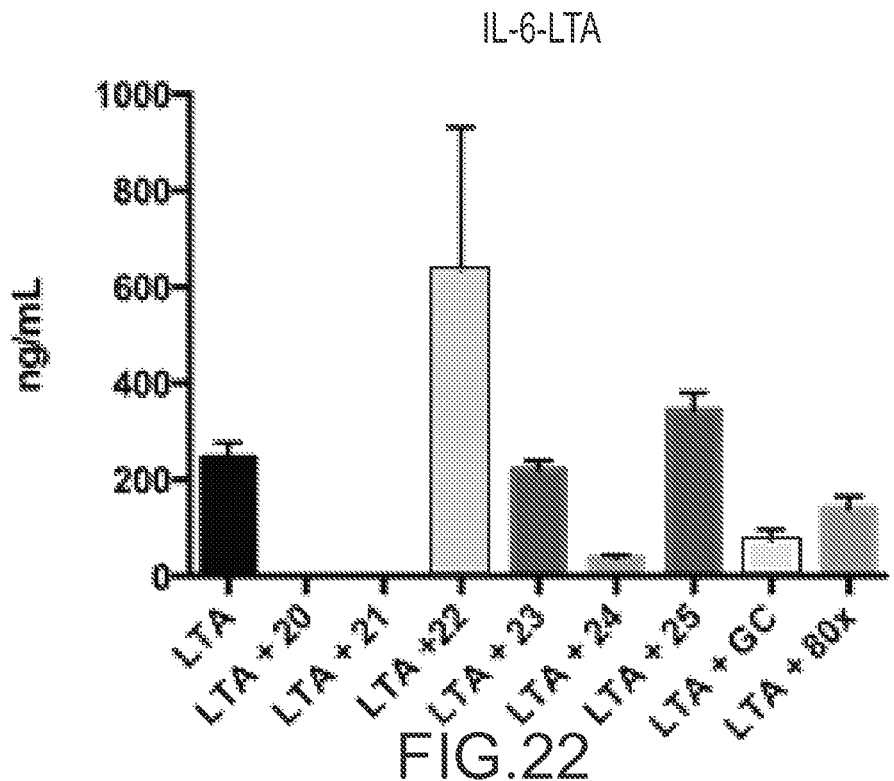
FIG. 22 shows a bar graph illustrating the efficacy of the method on the production of IL-6 in the presence of LTA according to various exemplary embodiments of the present invention.

Referring now to FIGS. 21 and 22, the effect of Compounds 20-25, GC and DC ("80×" in the figures) on the production and secretion of IL-6 from pBMEC was measured for cells stimulated with LPS (FIG. 21) or LTA (FIG. 22). For pBMEC stimulated with LPS, Compounds 20, 24 and GC suppressed IL-6 formation, whereas Compounds 22, 23, 25 and DC increased levels, relative to the control level of IL-6 found when cells were stimulated with LPS alone. For pBMEC stimulated with LTA, Compounds 20, 21, 24, GC and DC suppressed IL-6 formation, whereas Compounds 22 and 25 increased levels, relative to the control level of IL-6 found when cells were stimulated with LTA alone. Thus in various embodiments, select compounds derived from phyto-percolate or its fractions can be used to suppress IL-6 during inflammation, thus enabling the therapeutic benefits that may be derived therefrom.

Figure 23:
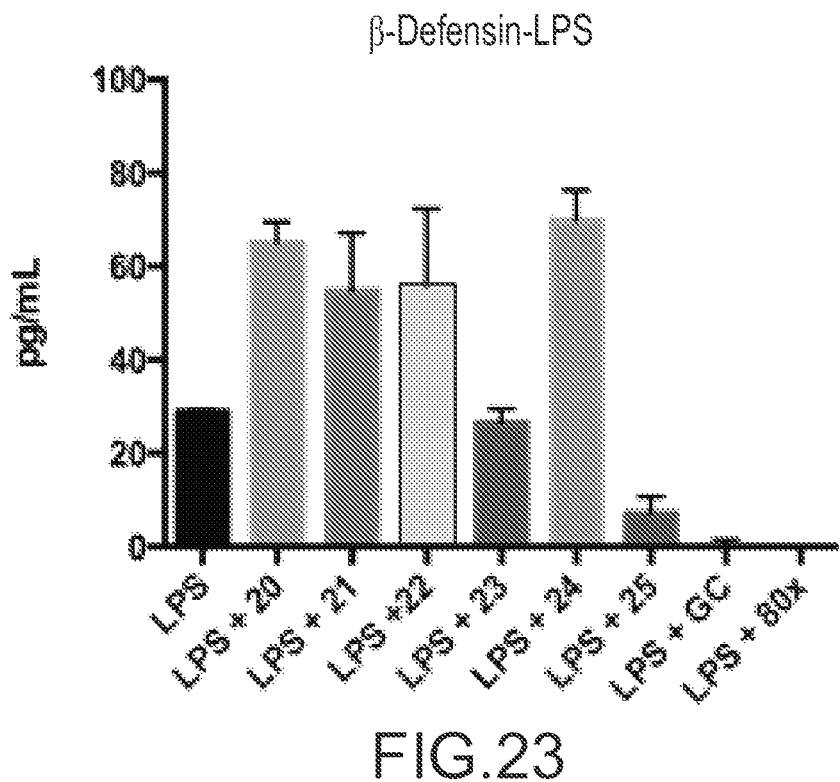
FIG. 23 shows a bar graph illustrating the efficacy of the method on the production of β-defensin in the presence of LPS according to various exemplary embodiments of the present invention.
Figure 24:
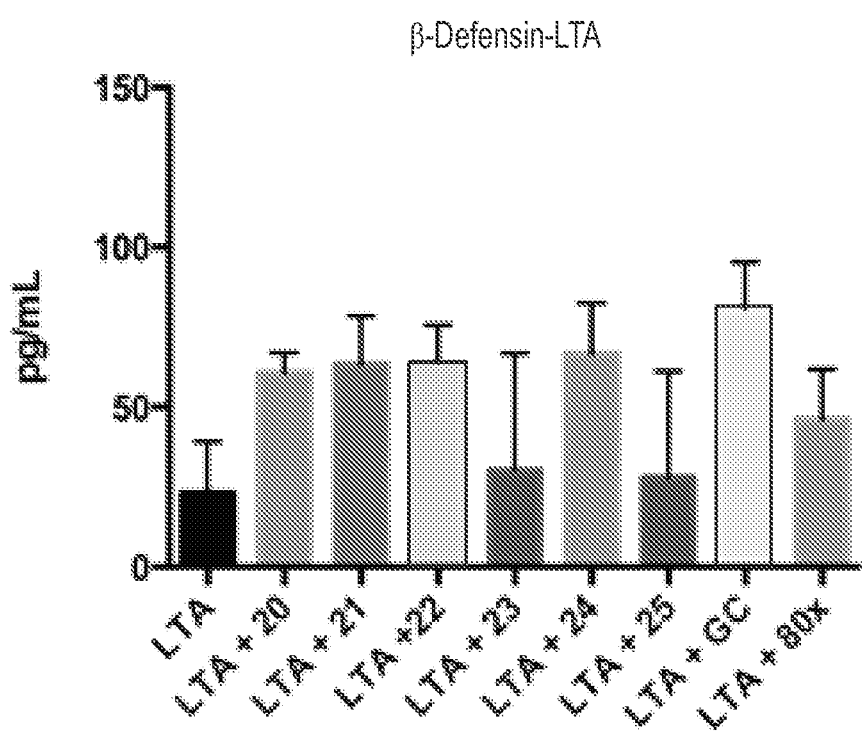
FIG. 24 shows a bar graph illustrating the efficacy of the method on the production of β-defensin in the presence of LTA according to various exemplary embodiments of the present invention.

Referring now to FIGS. 23 and 24, the effect of Compounds 20-25, GC and DC ("80×" in the figures) on the production and secretion of β-defensin from pBMEC was measured for cells stimulated with LPS (FIG. 23) or LTA (FIG. 24). For pBMEC stimulated with LPS, Compounds 25, GC and DC suppressed β-defensin formation, whereas Compounds 20, 21, 22, and 24 increased β-defensin levels, relative to the control level of β-defensin found when cells were stimulated with LPS alone. For pBMEC stimulated with LTA, Compounds 20, 21, 22, 24, GC and DC all increased β-defensin levels, relative to the control level of β-defensin found when cells were stimulated with LTA alone. Thus in various embodiments, select compounds derived from phyto-percolate or its fractions can be used to increase the antibacterial β-defensin during inflammation, thus enabling the therapeutic benefits that may be derived therefrom. Depending on the pathogenic stimulant, select compounds derived from phyto-percolate or its fractions can be used to increase β-defensin during inflammation, thus enabling the therapeutic benefits that may be derived therefrom.

In conclusion, isolates from cultures or co-cultures of specific freshwater microorganisms, algae, moss, bacteria and/or fungi have been shown to affect the levels of various pro-inflammatory and anti-inflammatory cytokines in epithelial cells stimulated with pathogens or pathogenic substances. In various embodiments, isolates and fractions from cultures or co-cultures of specific freshwater microorganisms, algae, moss, bacteria and/or fungi have been shown to affect the levels of various pro-inflammatory and anti-inflammatory cytokines produced in primary bovine mammary epithelial cells exposed to various pathogenic stimulants, thus demonstrating the use of said isolates and fractions in the treatment of bovine mastitis and in modulating the immune response in bovine mastitis and related infections and inflammations in animals and humans.

It should be understood that various principles of the invention have been described in illustrative embodiments. However, many combinations and modifications of the above-described formulation, proportions, elements, materials, and components used in the practice of the invention, in addition to those not specifically described, may be varied and particularly adapted to specific environments and operating requirements without departing from those principles. Other variations and modifications of the present invention will be apparent to those of ordinary skill in the art, and thus it is the intent that such variations and modifications be within the scope this disclosure.

The invention claimed is:

1. A method of treating mastitis in a cow, said method comprising administering to said cow a therapeutically effective amount of one or more of (a) a phyto-percolate isolate produced by culturing microorganisms of ATCC Deposit No. PTA-5863, wherein said isolate source is ABC Composite Lot #8 PAZ with a LC retention time of 3.29 minutes; 3.64 minutes, and MS (M+H; Daltons) 453; 679; (b) a phyto-percolate isolate produced by culturing microorganisms of ATCC Deposit No. PTA-5863, wherein said isolate source is Gelding Reserve PAZ with a LC retention time of 3.29 minutes; 3.64 minutes, and MS (M+H; Daltons) 453; 679; (c) a phyto-percolate isolate produced by culturing microorganisms of ATCC Deposit No. PTA-5863, wherein said isolate source is Gelding Reserve with a LC retention time of 3.29 minutes; 3.64 minutes, and MS (M+H; Daltons) 453; 679; (d) a phyto-percolate isolate produced by culturing microorganisms of ATCC Deposit No. PTA-5863, wherein said isolate source is Gelding reserve tank sample with a LC retention time of 3.29 minutes; 3.64 minutes, and MS (M+H; Daltons) 453; 679; and (e) a phyto-percolate isolate produced by culturing microorganisms of ATCC Deposit No. PTA-5863, wherein said isolate source is dilute ABC Composite Lot #8 PAZ with a LC retention time of 0.58 minutes; 2.43 minutes; 2.93 minutes; 3.14 minutes; 3.50 minutes; 3.78 minutes; 4.07 minutes; 4.35 minutes; 4.92 minutes; 5.14 minutes; 5.57 minutes; 6.99 minutes; 7.35 minutes; 7.63 minutes.

2. The method of claim 1, wherein the one or more isolates produced by culturing microorganisms of ATCC Deposit No. PTA-5863 up-regulate at least one anti-inflammatory cytokine in bovine mammary epithelial cells, and/or down-regulate at least one pro-inflammatory cytokine in bovine mammary epithelial cells.

3. The method of claim 2, wherein each of said cytokines is selected from the group consisting of TNF-α, lactoferrin, IFN-γ, IL-1β, serum amyloid-A (SAA), IL-6 and β-defensin.

4. A method of modulating an immune response in bovine, swine or canine, said method comprising the step of administering to said bovine, swine or canine an effective amount of one or more of (a) a phyto-percolate isolate produced by culturing microorganisms of ATCC Deposit No. PTA-5863, wherein said isolate source is ABC Composite Lot #8 PAZ with a LC retention time of 3.29 minutes; 3.64 minutes, and MS (M+H; Daltons) 453; 679; (b) a phyto-percolate isolate produced by culturing microorganisms of ATCC Deposit No. PTA-5863, wherein said isolate source is Gelding Reserve PAZ with a LC retention time of 3.29 minutes; 3.64 minutes, and MS (M+H; Daltons) 453; 679; (c) a phyto-percolate isolate produced by culturing microorganisms of ATCC Deposit No. PTA-5863, wherein said isolate source is Gelding Reserve with a LC retention time of 3.29 minutes; 3.64 minutes, and MS (M+H; Daltons) 453; 679; (d) a phyto-percolate isolate produced by culturing microorganisms of ATCC Deposit No. PTA-5863, wherein said isolate source is Gelding reserve tank sample with a LC retention time of 3.29 minutes; 3.64 minutes, and MS (M+H; Daltons) 453; 679; and (e) a phyto-percolate isolate produced by culturing microorganisms of ATCC Deposit No. PTA-5863, wherein said isolate source is dilute ABC Composite Lot #8 PAZ with a LC retention time of 0.58 minutes; 2.43 minutes; 2.93 minutes; 3.14 minutes; 3.50 minutes; 3.78 minutes; 4.07 minutes; 4.35 minutes; 4.92 minutes; 5.14 minutes; 5.57 minutes; 6.99 minutes; 7.35 minutes; 7.63 minutes, wherein said immune response is characteristic of bovine mastitis, bovine respiratory disease complex, transition cow syndrome, canine osteoarthritis, canine skeletal-muscular overexertion, or porcine reproductive and respiratory syndrome virus immune disorder.

5. The method of claim 4, wherein said immune response is triggered by the presence of at least one of *Staphylococcus aureus, Streptococcus uberis*, and *Escherichia coli*.

6. The method of claim 4, wherein the one or more isolates produced by culturing microorganisms of ATCC Deposit No. PTA-5863 up-regulate at least one anti-inflammatory cytokine, and/or down-regulate at least one pro-inflammatory cytokine involved in said immune response.

7. The method of claim 6, wherein each of said cytokines is selected from the group consisting of TNF-α, lactoferrin, IFN-γ, IL-1β, serum amyloid-A (SAA), IL-6 and β-defensin.

8. A method of promoting an antimicrobial response at a site of infection in an animal, said method comprising the step of administering to said animal an effective amount of one or more of (a) a phyto-percolate isolate produced by culturing microorganisms of ATCC Deposit No. PTA-5863, wherein said isolate source is ABC Composite Lot #8 PAZ with a LC retention time of 3.29 minutes; 3.64 minutes, and MS (M+H; Daltons) 453; 679; (b) a phyto-percolate isolate produced by culturing microorganisms of ATCC Deposit No. PTA-5863, wherein said isolate source is Gelding Reserve PAZ with a LC retention time of 3.29 minutes; 3.64 minutes, and MS (M+H; Daltons) 453; 679; (c) a phyto-percolate isolate produced by culturing microorganisms of ATCC Deposit No. PTA-5863, wherein said isolate source is Gelding Reserve with a LC retention time of 3.29 minutes; 3.64 minutes, and MS (M+H; Daltons) 453; 679; (d) a phyto-percolate isolate produced by culturing microorganisms of ATCC Deposit No. PTA-5863, wherein said isolate source is Gelding reserve tank sample with a LC retention time of 3.29 minutes; 3.64 minutes, and MS (M+H; Daltons) 453; 679; and (e) a phyto-percolate isolate produced by culturing microorganisms of ATCC Deposit No. PTA-5863, wherein said isolate source is dilute ABC Composite Lot #8 PAZ with a LC retention time of 0.58 minutes; 2.43 minutes; 2.93 minutes; 3.14 minutes; 3.50 minutes; 3.78 minutes; 4.07 minutes; 4.35 minutes; 4.92 minutes; 5.14 minutes; 5.57 minutes; 6.99 minutes; 7.35 minutes; 7.63 minutes.

9. The method of claim 8, wherein said animal is a cow.

10. The method of claim 9, wherein said site of infection is mammary tissue.

11. The method of claim 8, wherein said site of infection comprises the presence of *Staphylococcus, Streptococcus, Escherichia*, or *Mycoplasma* pathogens.

12. The method of claim 8, wherein the one or more isolates produced by culturing microorganisms of ATCC Deposit No. PTA-5863 up-regulate at least one anti-inflammatory cytokine, and/or down-regulate at least one pro-inflammatory cytokine within cells at said site of infection.

13. The method of claim 12, wherein each of said cytokines is selected from the group consisting of TNF-α, lactoferrin, IFN-γ, IL-1β, serum amyloid-A (SAA), IL-6 and β-defensin.

14. The method of claim 12, wherein said animal is a cow, said cells comprise bovine mammary epithelial cells, and said site of infection is bovine mammary tissue.

* * * * *